(12) United States Patent
Leach et al.

(10) Patent No.: US 11,783,240 B2
(45) Date of Patent: Oct. 10, 2023

(54) BUILDING MANAGEMENT SYSTEM WITH DYNAMIC WORKSPACE ASSIGNMENT

(71) Applicant: Johnson Controls Tyco IP Holdings LLP, Milwaukee, WI (US)

(72) Inventors: Matthew Leach, Cork (IE); Edward Gerard McNamara, County Limerick (IE); Rachel D. M. Ellerman, Shorewood, WI (US)

(73) Assignee: JOHNSON CONTROLS TYCO IP HOLDINGS LLP, Milwaukee, WI (US)

( * ) Notice: Subject to any disclaimer, the term of this patent is extended or adjusted under 35 U.S.C. 154(b) by 43 days.

(21) Appl. No.: 17/505,104

(22) Filed: Oct. 19, 2021

(65) Prior Publication Data

US 2022/0036258 A1 Feb. 3, 2022

Related U.S. Application Data

(63) Continuation-in-part of application No. 17/220,795, filed on Apr. 1, 2021, now Pat. No. 11,367,534.
(Continued)

(51) Int. Cl.
*G06Q 10/02* (2012.01)
*G16H 50/80* (2018.01)
(Continued)

(52) U.S. Cl.
CPC ............. *G06Q 10/02* (2013.01); *A61L 2/10* (2013.01); *A61L 2/24* (2013.01); *G06Q 30/08* (2013.01); *G16H 50/80* (2018.01)

(58) Field of Classification Search
CPC .......... G06Q 10/02; G06Q 30/08; A61L 2/10; A61L 2/24; G16H 50/80
See application file for complete search history.

(56) References Cited

U.S. PATENT DOCUMENTS 6,968,179 B1 11/2005 De Vries
7,099,895 B2 8/2006 Dempsey
(Continued)

FOREIGN PATENT DOCUMENTS

JP 2010-128976 A 6/2010
KR 20200047457 A 5/2020
WO WO-2021/258116 A1 12/2021

OTHER PUBLICATIONS

Condeco Group, "Meeting Room & Desk Booking Systems," URL: www.condecosoftware.com/, Retrieved from Internet Sep. 9, 2020, 10 Pages.
(Continued)

*Primary Examiner* — Hongmin Fan
(74) *Attorney, Agent, or Firm* — Foley & Lardner LLP

(57) ABSTRACT

A method for mitigating risk of transmission of a contagious disease in a building. The method includes determining, by a processing circuit including one or more processors, a safety rule to be applied to a workspace including a plurality of workspace stations, the safety rule relating to limiting the transmission of the contagious disease. The method includes receiving a request for one or more reservable workspace stations, the request including one or more request parameters. The method includes identifying the one or more reservable workspace stations from among the plurality of workspace stations by determining whether to permit the one or more reservable workspace stations to be reserved based on the safety rule. The method includes generating data identifying the one or more reservable workspace stations.

19 Claims, 17 Drawing Sheets

Related U.S. Application Data

(60) Provisional application No. 63/112,030, filed on Nov. 10, 2020, provisional application No. 63/004,269, filed on Apr. 2, 2020.

(51) Int. Cl.
    *G06Q 30/08*     (2012.01)
    *A61L 2/24*     (2006.01)
    *A61L 2/10*     (2006.01)

(56) References Cited

U.S. PATENT DOCUMENTS

| | | |
|---|---|---|
| 7,394,370 B2 | 7/2008 | Chan |
| 7,598,854 B2 | 10/2009 | Wong |
| 7,705,723 B2 | 4/2010 | Kahn et al. |
| 7,817,046 B2 | 10/2010 | Coveley et al. |
| 7,941,096 B2 | 5/2011 | Perkins et al. |
| 7,993,266 B2 | 8/2011 | Colston et al. |
| 8,049,614 B2 | 11/2011 | Kahn et al. |
| 8,405,503 B2 | 3/2013 | Wong |
| 8,867,993 B1 | 10/2014 | Perkins et al. |
| 9,075,909 B2 | 7/2015 | Almogy et al. |
| 9,741,233 B2 | 8/2017 | Laufer et al. |
| 10,068,116 B2 | 9/2018 | Good et al. |
| 10,198,779 B2 | 2/2019 | Pittman et al. |
| 10,251,610 B2 | 4/2019 | Parthasarathy et al. |
| 10,257,642 B2 | 4/2019 | Pittman et al. |
| 10,803,993 B2 | 10/2020 | Huang |
| 10,856,103 B2 | 12/2020 | Merjanian et al. |
| 2006/0036619 A1 | 2/2006 | Fuerst et al. |
| 2006/0085483 A1 | 4/2006 | Mooney et al. |
| 2009/0319765 A1 | 12/2009 | Fehrle |
| 2010/0333168 A1 | 12/2010 | Herrod |
| 2012/0056720 A1 | 3/2012 | Barvick et al. |
| 2014/0049376 A1 | 2/2014 | Ng |
| 2015/0176998 A1 | 6/2015 | Huang et al. |
| 2015/0257119 A1 | 9/2015 | Hahm et al. |
| 2015/0310490 A1 | 10/2015 | Meredith et al. |
| 2016/0005300 A1 | 1/2016 | Laufer et al. |
| 2016/0357422 A1 | 12/2016 | Milden et al. |
| 2017/0026897 A1 | 1/2017 | Hanson et al. |
| 2017/0123440 A1 | 5/2017 | Mangsuli et al. |
| 2017/0124850 A1 | 5/2017 | Kramer |
| 2017/0206334 A1 | 7/2017 | Huang |
| 2018/0048998 A1 | 2/2018 | Mahajan et al. |
| 2018/0052970 A1 | 2/2018 | Boss et al. |
| 2018/0091939 A1 | 3/2018 | Venkatraman et al. |
| 2018/0104162 A1 | 4/2018 | Park |
| 2018/0204162 A1 | 7/2018 | Endel et al. |
| 2019/0029056 A1 | 1/2019 | Hor-Lao et al. |
| 2019/0196424 A1 | 6/2019 | Meganathan et al. |
| 2019/0228348 A1 | 7/2019 | O'Keefe-Sally et al. |
| 2020/0167148 A1 | 5/2020 | Park et al. |
| 2020/0176124 A1 | 6/2020 | Chatterjea et al. |
| 2020/0176125 A1 | 6/2020 | Chatterjea et al. |
| 2021/0051444 A1 | 2/2021 | Ryu et al. |
| 2021/0158675 A1 | 5/2021 | Burris et al. |
| 2021/0193309 A1 | 6/2021 | Boisvert et al. |
| 2021/0313075 A1 | 10/2021 | Mc Namara et al. |
| 2021/0374620 A1* | 12/2021 | Tokuchi ............... G06Q 10/109 |
| 2021/0390807 A1 | 12/2021 | Chaurasia et al. |
| 2021/0390812 A1 | 12/2021 | Chaurasia et al. |
| 2021/0391089 A1 | 12/2021 | Eswara et al. |
| 2021/0398659 A1 | 12/2021 | Sharma et al. |
| 2021/0398690 A1 | 12/2021 | Gibson et al. |
| 2021/0398691 A1 | 12/2021 | Dhamija et al. |
| 2022/0060856 A1 | 2/2022 | Wellig et al. |

OTHER PUBLICATIONS

Condeco, "Back to the new normal," 2020, 12 Pages.
Condeco, "How tomorrow will work: returning to the office after COVID-19 Guide," URL: https://www.condecosoftware.com/modern-workplace/asset/ebooks/returning-to-the-office-after-covid-19-guide/, Retrieved from Internet Dec. 14, 2021, 8 Pages.
Condeco, "Making your employees safety a priority when coming into the office," URL: https://www.condecosoftware.com/blog/employee-office-safety/, Sep. 27, 2020, 5 Pages.
Condeco, "Office layouts for the post COVID-19 workplace," URL: https://www.condecosoftware.com/blog/office-design-post-covid-19-workplace/, Jun. 25, 2020, 6 Pages.
Condeco, "Putting your employees health and well-being first—post-pandemic mental health tips," URL: https://www.condecosoftware.com/blog/employee-health-well-being-post-pandemic/, Sep. 17, 2020, 5 Pages.
Condeco, "Rethinking and reshaping your workspace," URL: https://www.condecosoftware.com/blog/rethinking-reshaping-workspace/, May 27, 2021, 5 Pages.
Condeco, "Returning to the office after COVID-19." URL: https://www.condecosoftware.com/modern-workplace/wp-content/uploads/sites/10/2020/05/TL-SOL-226-EN_Returning-to-the-office-after-COVID-19.pdf, Retrieved from Internet Dec. 14, 2021, 23 Pages.
Condeco, "Returning to the Office Post COVID-19: and why businesses can't afford to get this wrong.," URL:https://www.condecosoftware.com/blog/returning-to-the-office-post-covid-19/, May 6, 2020, 5 Pages.
Condeco, "Safe social distancing measures on your return to the office," URL: https://www.condecosoftware.com/blog/safe-office-social-distancing-measures/, May 26, 2020, 6 Pages.
Condeco, "The future of the workplace and effective workspace scheduling," URL: https://www.condecosoftware.com/blog/future-workspace-scheduling/, Oct. 24, 2020, 5 Pages.
Condeco, "The post-COVID workplace." URL: https://www.condecosoftware.com/modern-workplace/asset/ebooks/post-covid-workplace/, Retrieved from Internet Dec. 14, 2021, 7 Pages.
Condeco, "The work-related COVID-19 questions we're all asking," URL: https://www.condecosoftware.com/blog/work-related-covid-questions/, Oct. 29, 2020, 5 Pages.
Condeco, "What's next? Your work life after COVID-19," URL: https://www.condecosoftware.com/blog/work-life-after-covid/, Jul. 27, 2021, 5 Pages.
Condeco, "Workplace cleanliness: The facts for a post-isolation working environment," URL: https://www.condecosoftware.com/blog/workplace-cleanliness-facts/, Apr. 23, 2020, 6 Pages.
OfficeSpace Software, "OfficeSpace Software: The Smarter Facility Management Software," URL: www.officespacesoftware.com/, Retrieved from Internet Sep. 9, 2020, 5 Pages.

* cited by examiner

BUILDING MANAGEMENT SYSTEM WITH DYNAMIC WORKSPACE ASSIGNMENT

CROSS-REFERENCE TO RELATED APPLICATIONS

This Application is being filed as a Continuation-In-Part of U.S. Non-Provisional application Ser. No. 17/220,795, filed Apr. 1, 2021, which claims the benefit and priority to U.S. Provisional Application No. 63/004,269, filed Apr. 2, 2020, and Indian Provisional Application No. 202011032928, filed Jul. 31, 2020, which are incorporated herein by reference in their entirety. This Application also claims the benefit and priority to U.S. Provisional Application No. 63/112,030, filed Nov. 10, 2020.

BACKGROUND

The present disclosure relates to workspace reservation systems. More specifically, according to some embodiments, the present disclosure relates to workspace booking systems that allow workers flexibility in reserving workspaces while enforcing certain workspace usage rules, such as social distancing rules.

Infectious diseases, such as COVID-19, cause challenges for establishing a safe working environment. Working environments such as shared workspaces in which workers are seated in close proximity to one another for substantial amounts of time can increase the risk of spread of illness. Additionally, as organizations adapt to such challenges, there may be a desire for more flexible workspaces that allow for workers to reserve workspaces as needed, rather than have a permanently dedicated workspace that may or may not be used at a particular time. There is a need for a system that allows for such flexible workplace scheduling while providing for enforcement of workspace usage rules.

SUMMARY

One implementation of the present disclosure is a method for mitigating risk of transmission of a contagious disease in a building. The method includes determining, by a processing circuit including one or more processors, a safety rule to be applied to a workspace including a plurality of workspace stations, the safety rule relating to limiting the transmission of the contagious disease. The method includes receiving, at the processing circuit, a request for one or more reservable workspace stations, the request including one or more request parameters. The method includes identifying the one or more reservable workspace stations from among the plurality of workspace stations by determining, by the processing circuit, whether to permit the one or more reservable workspace stations to be reserved based on the safety rule. The method includes generating, by the processing circuit, data identifying the one or more reservable workspace stations.

In some embodiments, determining the safety rule to be applied to the workspace includes determining a safety threshold based on at least one of a period of time since a hazardous incident has occurred at the workplace station, a risk level associated with the contagious disease, and an amount of sanitization that was performed at the one of the plurality of workplace station.

In some embodiments, the one or more request parameters includes a timing parameter, and the safety rule includes a threshold amount of time the workspace stations must be unoccupied after a last occupant. In some embodiments, identifying the reservable workspace stations includes determining that the workspace station has been unoccupied for at least the threshold amount of time.

In some embodiments, the safety rule further includes a requirement that adjacent workstations or workstations within a threshold distance of one another must be unoccupied for the threshold amount of time for the workstations to be reservable.

In some embodiments, the safety rule is based on occupancy of adjacent workstations or workstations within a threshold distance of one another. In some embodiments, the safety rule includes prohibiting reservation of a workspace station based on an adjacent/proximal workspace station being occupied at the time for which the reservation is requested.

In some embodiments, determining whether to permit the workspace stations to be reserved based on the safety rule includes determining that the one or more workspace stations are not reservable based on the safety rule, and implementing an automated sanitizing feature or a notification to a building occupant to sanitize the one or more workspace stations such that the one or more workspace stations are reservable. In some embodiments, the automated sanitizing feature includes at least one of sanitizing light or ultraviolet violet (UV) A light, UVB light, or UVC light.

In some embodiments, the method further includes generating graphical user interface (GUI) data that provides visual indicators to a GUI to indicate whether the workspace stations are reservable or not reservable.

In some embodiments, determining whether to permit the workspace stations to be reserved based on the safety rule includes determining at least one of an indication of the reason for the restriction and a time in which the restriction will be lifted and providing the at least of the indication and the time to the GUI.

In some embodiments, determining at least one of the indication and the time in which the restriction will be lifted includes determining whether the time in which the restriction will be lifted has occurred or will occur, wherein in response to determining the time has occurred, provide a first notification to the GUI and, in response to determining the time will occur, provide a second notification to the GUI.

In some embodiments, the method further includes generating, by the processing circuit, a price for reserving the one or more reservable workspace stations, providing the price and the one or more reservable workspace stations to a user interface, receiving, via the user interface, an input indicating a payment satisfying the price, and, in response to receiving the payment, satisfying the request to reserve the one or more reservable workplace stations.

In some embodiments, generating the price for reserving the one or more reservable workspace stations includes receiving a plurality of bids for the one or more reservable workspace stations, wherein each of the plurality of bids is provided using a corresponding user interface and updating the price based on the number of received bids of the plurality of bids.

In some embodiments, receiving the request for one or more reservable workspace stations includes receiving the request for one or more reservable workplace stations located in a location separate from the building, wherein the one or more reservable workspace stations are reservable to the employees of the building.

Another implementation of the present disclosure is a non-transitory computer-readable storage media having computer-executable instructions stored thereon that, when executed by one or more processors, cause the one or more processors to perform. The operations include determining, by a processing circuit including one or more processors, a safety rule to be applied to a workspace including a plurality of workspace stations, the safety rule relating to limiting the transmission of the contagious disease, receiving, at the processing circuit, a request for one or more reservable workspace stations, the request including one or more request parameters, identifying the one or more reservable workspace stations from among the plurality of workspace stations by determining, by the processing circuit, whether to permit the one or more reservable workspace stations to be reserved based on the safety rule, and generating, by the processing circuit, data identifying the one or more reservable workspace stations.

In some embodiments, receiving the request for one or more reservable workspace stations includes receiving the request for one or more reservable workplace stations located in a location separate from the building, wherein the one or more reservable workspace stations are reservable to the employees of the building.

In some embodiments, determining the safety rule to be applied to the workspace includes determining a safety threshold based on at least one of a period of time since a hazardous incident has occurred at the workplace station, a risk level associated with the contagious disease, and an amount of sanitization that was performed at the one of the plurality of workplace station.

In some embodiments, the one or more request parameters includes a timing parameter. In some embodiments, the safety rule includes a threshold amount of time the workspace stations must be unoccupied after a last occupant. In some embodiments, identifying the reservable workspace stations includes determining that the workspace station has been unoccupied for at least the threshold amount of time.

In some embodiments, the one or more processors are further configured to generate the price for reserving the one or more reservable workspace stations, provide the price and the one or more reservable workspace stations to a user interface, receive, via the user interface, an input indicating a payment satisfying the price, and, in response to receiving the payment, satisfy the request to reserve the one or more reservable workplace stations.

In some embodiments, generating the price for reserving the one or more reservable workspace stations includes receiving a plurality of bids for the one or more reservable workspace stations, wherein each of the plurality of bids is provided using a corresponding user interface and updating the price based on the number of received bids of the plurality of bids.

Another implementation of the present disclosure is a system for mitigating risk of transmission of a contagious disease in a building, the system including a processing circuit including one or more processors and memory that, when executed by the one or more processors, causes the one or more processors to perform operations including determining a safety rule to be applied to a workspace including a plurality of workspace stations, the safety rule relating to limiting the transmission of the contagious disease, receiving a request for one or more reservable workspace stations, the request including one or more request parameters, identifying the one or more reservable workspace stations from among the plurality of workspace stations by determining, by the processing circuit, whether to permit the one or more reservable workspace stations to be reserved based on the safety rule, and generating data identifying the one or more reservable workspace stations.

In some embodiments, the processing circuit is further configured to generate, by the processing circuit, a price for reserving the one or more reservable workspace stations, provide the price and the one or more reservable workspace stations to a user interface, receive, via the user interface, an input indicating a payment satisfying the price, and, in response to receiving the payment, satisfy the request to reserve the one or more reservable workplace stations.

BRIEF DESCRIPTION OF THE DRAWINGS

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

DETAILED DESCRIPTION

Overview

In various situations where workers (e.g., building occupants, etc.) are required to work from home for prolonged periods of time due to epidemiological factors (e.g., COVID-19, etc.), certain instances may arise where workers need to come into work at intermittent periods. For example, a worker designated to work from home may need to come into work once or twice a week for various meetings. In some embodiments, workers may need to reserve their working spaces (e.g., desks, chairs, workstations, etc.) situations where entry into a workplace building is unpredictable, workers may need to reserve their working space prior to entering the workplace building.

As described herein, multiple instances of office desks, workplace stations, workspaces, areas, and work locations are described, which may be used interchangeably. As generally described herein, all types of locations where a building occupant may perform tasks are considered. These include individual desks, offices, cubicles, tables, booths, and couches. These locations are located within a workspace (e.g., building 10) and may be described as workplace stations, workspace stations, and other titles. In some embodiments, these workspaces part of another building. For example, an employee of building 10 may reserve a workspace in a separate building. This systems and methods disclosed herein may incorporate the systems and methods disclosed in U.S. Provisional Patent Application 63/004,269 filed Apr. 2, 2020, the entire disclosure of which is incorporated by reference herein.

Infection Transmission Risk Management

Figure 1:
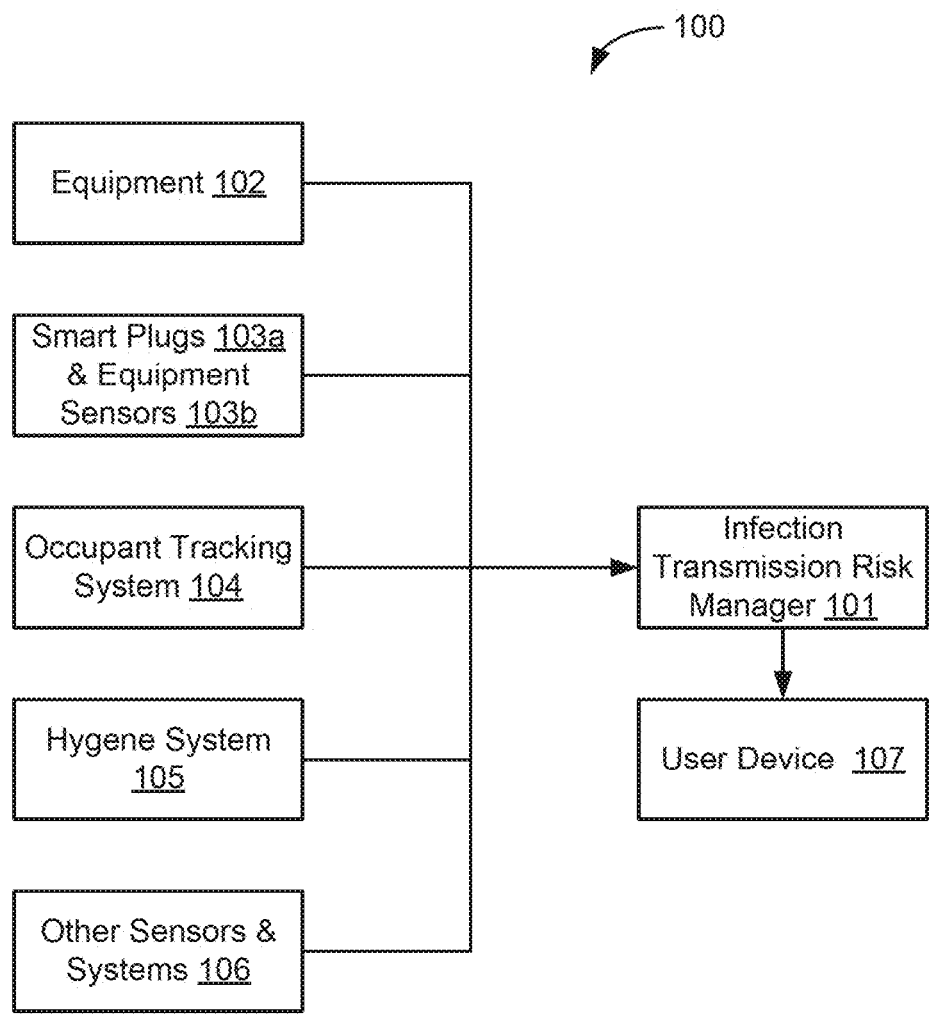
FIG. 1 is a block diagram of a system for managing infection risk within a monitored area, according to an exemplary embodiment.

Referring now to FIG. 1, a block diagram of a system 100 for infection transmission risk management of a building or other monitored area is shown, according to an exemplary embodiment. A monitored area may include an office, hospital, research laboratory, industrial, or commercial space, or any other shared space in which a monitoring of infection transmission risk is required. The monitored area may include various equipment that may be used by or interacted with by building occupants. To provide a method of managing infection transmission risk of persons to other persons through direct person-to-person interaction, indirect transmission through sharing of spaces, and potential contamination of common surfaces, system 100 monitors the location and use of equipment, and the location of individuals and their interactions with different people, spaces, and equipment, to support social distancing recommendations and infection risk management practices in response to a current disease epidemic, to assess and record transmission risk events, and to track and record interactions and locations for the purposes of contact tracing. As described in detail herein, system 100 is configured to receive various types of data from various types of data sources, process the data to identify possible contagion transfer risk for occupants, spaces, and equipment, generate social distancing risk events, contact tracing data and histories, risk analysis, and disinfection or cleansing data, and generate alerts, notifications, reports, and various graphical user interfaces displaying and reporting this information. System 100 thereby provides technical improvements to infection transmission risk management and assessment, by providing responses to transmission risk events, assisting an operation in more effectively managing the transmission risks associated with an infectious disease.

As shown in FIG. 1, the system 100 includes an infection transmission risk manager 101, equipment 102 communicable with the infection transmission risk manager 101, smart outlets and equipment sensors 103A and 103B communicable with the infection transmission risk manager 101, occupant tracking system 104 communicable with the infection transmission risk manager 101, hygiene system 105 communicable with the infection transmission risk manager 101, and other sensors and systems 106 communicable with the infection transmission risk manager 102. The system 100 is also shown to include a user device 107 communicable with the infection transmission risk manager 101.

Equipment 102 may include various devices that are used by occupants of the monitored area in the course of their work or occupation. For example, in a laboratory, equipment 102 may include centrifuges, microscopes, x-ray diffraction units, mass spectrometers, chemical processing equipment, computing resources (supercomputers, servers, etc.), incubators, and imaging systems, among many other possibilities depending on the research goals and particular scientific focus (e.g., pharmaceutical, biotechnology, food science, physics, etc.) of the laboratory. In a hospital space, equipment 102 may include ventilators, life monitoring devices, and other devices and equipment for the treatment of patients and conduct of hospital activities. In an office space, equipment 102 may include photocopiers, vending machines, conference telephones, monitors, displays, etc.

In some embodiments, the equipment 102 is configured to collect data relating to operation of the equipment 102. For example, a device of equipment 102 may be configured to store a log of when the device is turned on/off, how long the device is used for, what functions the device is commanded to perform, etc. In such a case, the equipment 102 obtains operating data that describes when the equipment 102 is in-use (operating, active, executing a task, etc.) or out-of-use (off, idle, etc.). The equipment 102 may be communicable with the infection transmission risk manager 101 (e.g., via information technology network (e.g., Ethernet, Wi-Fi, etc.) or a building network (e.g., BACNet, MSTP, etc.) to provide the operating data to the infection transmission risk manager 101.

The equipment 102 may consume one or more utility resources (e.g., electricity, natural gas, water, etc.) or specialty resources (distilled water, specialty chemicals, radioactive materials, liquid nitrogen, atmospheric gases, life support gases, office equipment consumables, such as printer ink and toner, etc.). In some embodiments, the equipment 102 is configured to measure the resource consumption of the equipment 102. The amount or rate of resource consumption may correspond to a status of the equipment 102. For example, a device of equipment 102 may consume a first amount of electricity when in an idle or off state, a second amount of electricity during start-up of the device or during configuration of a task for the device, and a third amount of electricity while performing a primary function of the device (e.g., executing a task, etc.). The different amounts may be known, experimentally-determinable, or determinable by employing machine learning methods, such that they can be used to determine the status of the equipment 102. Various statuses are possible depending on the functionality of a given device. Although the examples herein are described primarily in terms of electrical power consumption, it should be understood that embodiments using measurements of any other type of resource consumed by equipment are also within the scope of the present disclosure.

Equipment 102 may draw electricity from a building electrical system via smart plugs 103A. In the example shown, the smart plugs 103A are configured to be placed between a standard electrical outlet (e.g., wall outlet) and a power cord for a device of equipment 102. The smart plugs 103A can thereby be used with the system 100 without requiring any modification or specialization of the building electrical system. In other embodiments, the functions attributed herein to the smart plugs 103A may be performed by an element of the building electrical system (e.g., smart wall outlets, etc.).

Each smart plug 103A is configured to measure the amount or rate of electrical power passing therethrough to obtain a time series of electrical power measurements ("power consumption data") and to transmit the power consumption data to the infection transmission risk manager 101. The power consumption data may include both an amount or rate of electrical power consumption and a time stamp associated with that amount or rate. The smart plugs 103A may be communicable with the infection transmission risk manager 101 via a wireless network, for example a Wi-Fi network or cellular network.

Equipment 102 may also be fit with equipment sensors 103B configured to detect an interaction with or use of equipment 102. For example, a door of a refrigeration unit may be equipped with a sensor that detects when it has been opened or closed. Equipment sensors 103B may be communicable with the infection transmission risk manager 101 via a wireless network, for example a Wi-Fi network or cellular network.

The occupant tracking system 104 is configured to track occupants (people) in the monitored area. Various types of occupant tracking systems 104 are included in various embodiments. For example, in some embodiments the occupant tracking system 104 is implemented as part of an access and security system, in which a user can enter or exit a space by presenting a badge to an electronic card reader (e.g., RFID, magnetic stripe, etc.). The occupant tracking system 104 may monitor occupant locations based on entry into various secure spaces.

In other embodiments, the occupant tracking system 104 includes multiple beacons, with each beacon associated with an occupant, and a set of transceivers configured to determine the locations of the beacons. The beacons may be formed as Bluetooth Low Energy (BLE) badges, Ultra-wideband (UWB) badges, or badges using a similar radio communications technology, which may be worn or carried by personnel in the monitored area. The transceivers may be arranged around the monitored area. Each transceiver is configured to detect the presence of the beacons and determine a distance from a beacon to the transceiver. Based on the distance of a beacon to three or more transceivers (trilateration or triangulation), the location of the beacon can be determined with a high degree of accuracy. Such a system allows for occupant tracking across spaces regardless of whether the spaces are separated by walls or doors and to precisely locate occupants within a space.

In other embodiments, the occupant tracking system 104 includes devices monitoring person-to-person proximity events, e.g., smartphones running an app that determines proximity through strength of Bluetooth signals, Wi-Fi signals, sonic pings, or other method.

Hygiene system 105 may include dispenser devices configured to provide washing or disinfectant agents for the purposes of hand washing support and such dispenser devices may be equipped with sensors indicating levels of washing or disinfectant agent present in a device. Hygiene system may further include hygiene monitoring devices and systems configured to monitor compliance with recommended hygiene operations, such as whether a hand washing operation was carried out or whether a person complied with a correct hand washing technique and duration. Hygiene system 105 and the devices thereof may be communicable with the infection transmission risk manager 101 via a wireless network, for example a Wi-Fi network or cellular network.

The system 100 is also shown as including other sensors and systems 106. The other sensors and system 106 may provide various data relating to occupancy of the space or usage of equipment 102 in various ways. For example, a calendaring or scheduling system may be included that provides information about meeting times, holidays, event schedules, which may be relevant to analyzing space utilization. As another example, other sensors that measure usage or inventory may be included, for example a smart toilet sensor that measures a number of flushes and provides such information to the infection transmission risk manager 101. As yet another example, other sensors that measure interaction of a person with a device of equipment 102 may be included, for example, pressure or motion sensors detecting removal of a piece of equipment 102 from a location, etc. The present disclosure contemplates inclusion of any such available data in various embodiments.

The infection transmission risk manager 101 is configured to receive equipment operating data from the equipment 102 and/or the smart plugs 103A and equipment sensors 103B, occupancy data from the occupant tracking system 104, hygiene consumables and compliance data from the hygiene system 105, and, in some embodiments, other usage-related data from the other sensors and systems 106. The infection transmission risk manager 101 may associated the data points with one or more of multiple people, equipment, or spaces of the monitored area. The infection transmission risk manager 101 is also configured to process the data to determine an equipment usage and transmission risk data, a space usage and transmission risk data, an occupant presence and/or location data, an occupant infection transmission risk data in respect of person-to-person direct contact, indirect transmission risk due to shared use of equipment or spaces within a monitored area, and an occupant social distancing guideline breach. The infection transmission risk manager 101 is also configured to generate a graphical user interface illustrating transmission risk alerts, social distancing guideline breaches, risk ratings for people, spaces, or equipment, and to cause the user device 107 (e.g., smartphone, laptop, desktop computer, etc.) to display the graphical user interface. These and other features are described in detail below.

Figure 2:
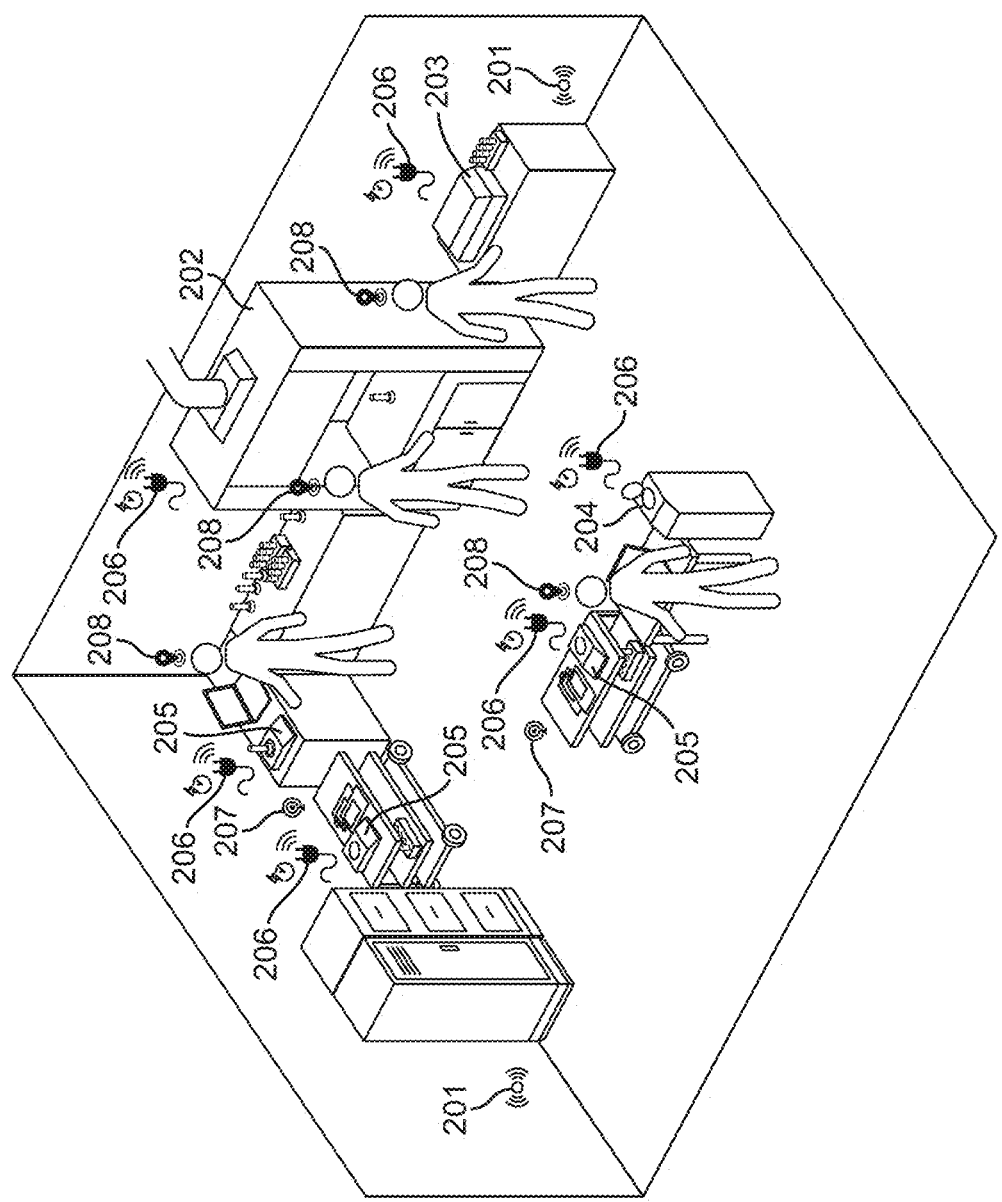
FIG. 2 is a perspective view of a monitored space of a monitored area served by the system of FIG. 1, according to an exemplary embodiment.

Referring now to FIG. 2, a perspective view of an example space within a monitored area served by system 100. In this example, the space is used as a laboratory, however systems and methods described in the present disclosure may also apply to other settings, such as hospital or medical facilities, including field hospitals, retail, industrial or manufacturing facilities, data centers, or commercial office spaces. In this example, the space is geofenced using sensors 201 (e.g., Bluetooth Low Energy (BLE) or Ultra-wideband (UWB) transceivers) included with occupant tracking system 104. The sensors 201 are arranged to provide occupant detection around a perimeter of the space. FIG. 2 also shows various equipment 102, including a fume hood 202, water bath 203, centrifuge 204, and scales 205.

These devices of equipment 102 are connected to smart plugs 103A. In the embodiment shown, mobile equipment (e.g., scales 205 in FIG. 2) includes a location tag 207 (e.g., a BLE or UWB beacon) which can be tracked by the sensors 201 of the occupant tracking system, for example to determine which space the mobile equipment is in at a given time. The occupants are shown to be carrying locations tags 208 (e.g., BLE or UWB badges) which can be triangulated using data from the sensors 201 of the occupant tracking system 104. The array of sensors, trackers, plugs, equipment, etc. provides an example of the hardware which may be included in a monitored area, such as laboratory, to facilitate the utilization monitoring described herein.

Figure 3:
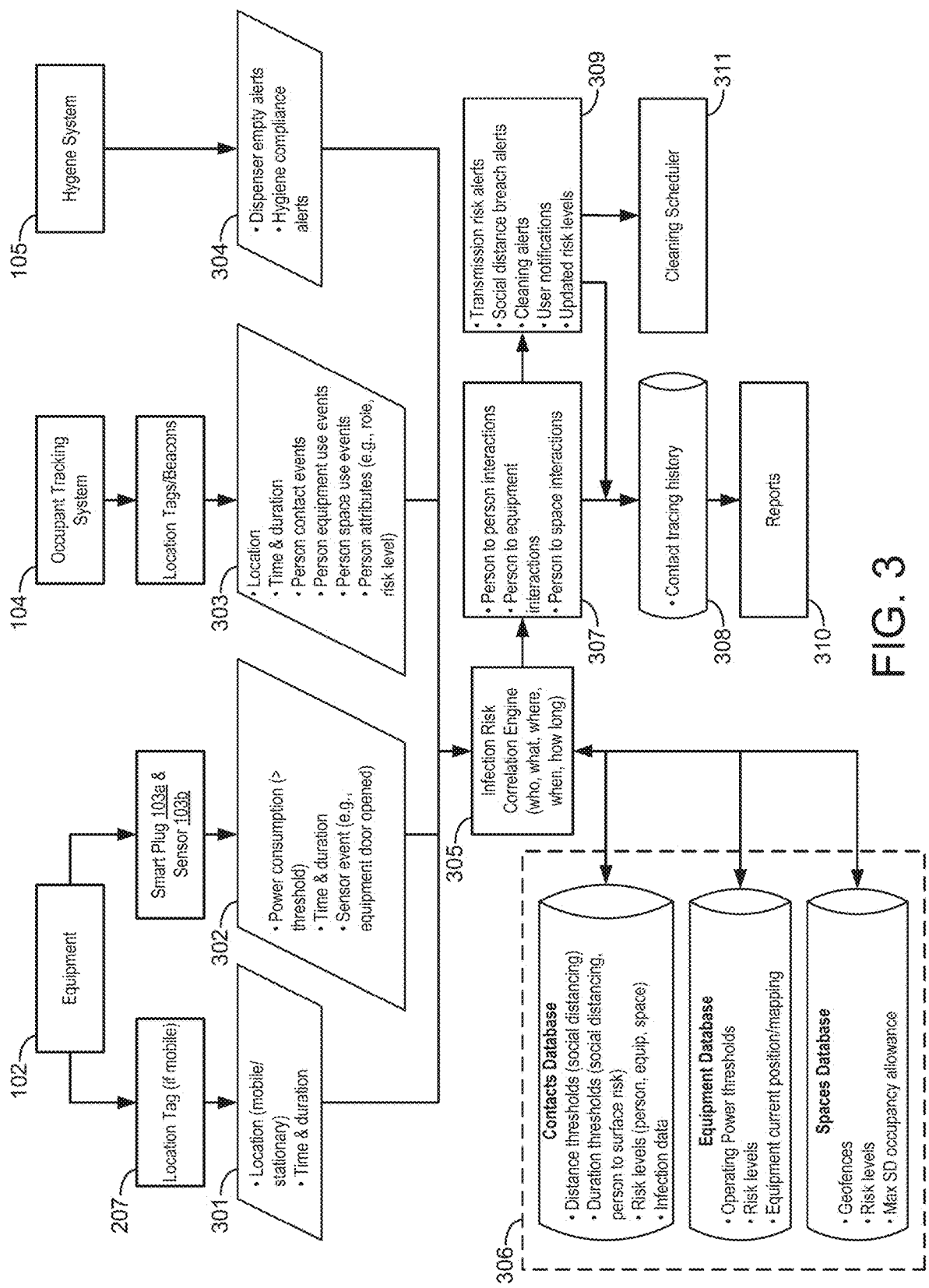
FIG. 3 is a schematic diagram of one example of the system of FIG. 1, according to an exemplary embodiment.

Referring now to FIG. 3, a schematic illustrating the elements of the system 100 and the data transfers and associations there is shown, according to an exemplary embodiment. As illustrated by FIG. 3, equipment 102 is connected to a smart plug and, where applicable, sensors indicating interactions with the equipment (e.g., door sensor on an equipment device) 103A and 103B, and, in the embodiment shown, to a location tag (e.g., location tag 207 of FIG. 2). The location tag is used, as shown in block 301, to provide data relating to the location of the equipment 102 and a time and duration relating to such equipment 102. That is, the data at block 301 may include locations of the equipment associated with time stamps, such that the amount of time the equipment 102 spends in any particular space can be ascertained. The smart plug 103A is shown to provide power consumption data and time and duration relating to such power consumption (e.g., a time series of power consumption values) at block 302. In some embodiments, the smart plug 103A only reports the power consumption when the power consumption is above a threshold value. The smart plug 103A may be configured to provide an identification code or other information that associates a particular smart plug 103A (and the data provided thereby) with a particular unit of equipment 102. The equipment sensor 103B may be configured to report an interaction of a person with the equipment, for example, a door sensor on a refrigeration unit. Sensor 103B may report its location data and time and duration of a sensor state. Power consumption data and sensor data may be used by the system 100 to determine that equipment is or is not in use.

FIG. 3 also shows that occupant tracking system 104 provides locations of occupants, the time and duration associated with such locations, attributes of the occupants (e.g., role, job title, risk level etc.), person contact events with persons, equipment, and spaces at block 303. The occupant tracking system 104 thereby provides the information needed to assess the number of people who used a space over a time period, and the types of persons that utilized the space. For example, researchers, janitors, interns, senior management, people with high, medium, or low risk levels, and different groups within a hospital or laboratory scenario, such as medical staff working with contagious patients and those working with non-contagious patients, or laboratory staff working near contagions, etc.

FIG. 3 also shows that a hygiene system 105 provides data about dispenser device empty alerts and hygiene compliance alerts at block 304.

As illustrated in FIG. 3, the data from block 301, block 302, block 303, and block 304 are provided to infection risk correlation engine 305. The infection risk correlation engine 305 may be executed by the infection transmission risk manager 101 of FIG. 1. As shown in FIG. 3, the infection risk correlation engine 305 may also receive various pre-stored parameters from various databases 306 of the infection transmission risk manager 101 of FIG. 1. The databases 306 are shown as specifying data about contacts, equipment, and spaces. For example, spaces database may contain one or more geofenced spaces (e.g., defined based on a boundary of such a space), space risk level ratings, maximum number of occupants under normal conditions, and maximum number of occupants under contagion conditions (derived from maximum social distancing allowances). Contacts database may contain social distancing time and duration thresholds, contact risk levels associated with person-to-person contacts, or person-to-surface or person space use contacts, and data about infection, such as incubation periods, infectivity periods, transmission dynamics, risk factor data, or immunity data. Equipment database may contain information about equipment such as operating power thresholds (below which an equipment may be determined to be not in use, such as when in an idle or sleep mode), equipment infection risk levels (e.g., a piece of equipment may, by its nature and use, be more at risk of contamination or, conversely, may have a low risk of contamination.), and equipment current position or mapped location within the monitored area. The parameters in the databases 306 can be configured/edited by a user to facilitate operation of the infection risk correlation engine 305 and, additionally, may be updated by the outputs of the infection risk correlation engine 305.

The infection risk correlation engine 305 may use the input data described above to determine various events, alerts, or insights, such as person-to-person interactions giving rise to transmission risk alerts or that are used for contact tracing histories. In addition, infection risk correlation engine may use input data to determine events, alerts, or insights in respect of contamination of equipment or spaces, based on detected uses or interactions of tracked individuals. Such information may similarly be used for contract tracing. Infection risk correlation engine 305 may generate alerts, such as social distancing breach alerts, infection transmission alerts, cleaning alerts, user notifications, and updated risk levels for people, equipment, and spaces. In addition, infection risk correlation engine 305 may receive data inputs from hygiene system 105 in respect of cleaning data from a hygiene system including cleansing fluid dispensers and hand washing monitors. Such data may include alerts that a dispenser is empty or alerts of a hygiene compliance issue. Infection correlation engine may use these data inputs to update risk levels for persons, equipment, or spaces and may generate targeted cleaning alerts to a cleaning scheduler or other system. Infection risk correlation engine may cause a contact tracing history database to be updated and reports of contact tracing generated. Infection risk correlation engine may, additionally, cause one or more notifications to occupants concerning risky contacts or social distancing breaches. Illustrations of the outputs of infection risk correlation engine 305 described above are indicated by block 307, block 308, block 309, block 310, and block 311.

Detecting Person-to-Person Contacts

One implementation of the present disclosure is a method of detecting interactions between people that create a risk of person-to-person infection.

Figure 4:
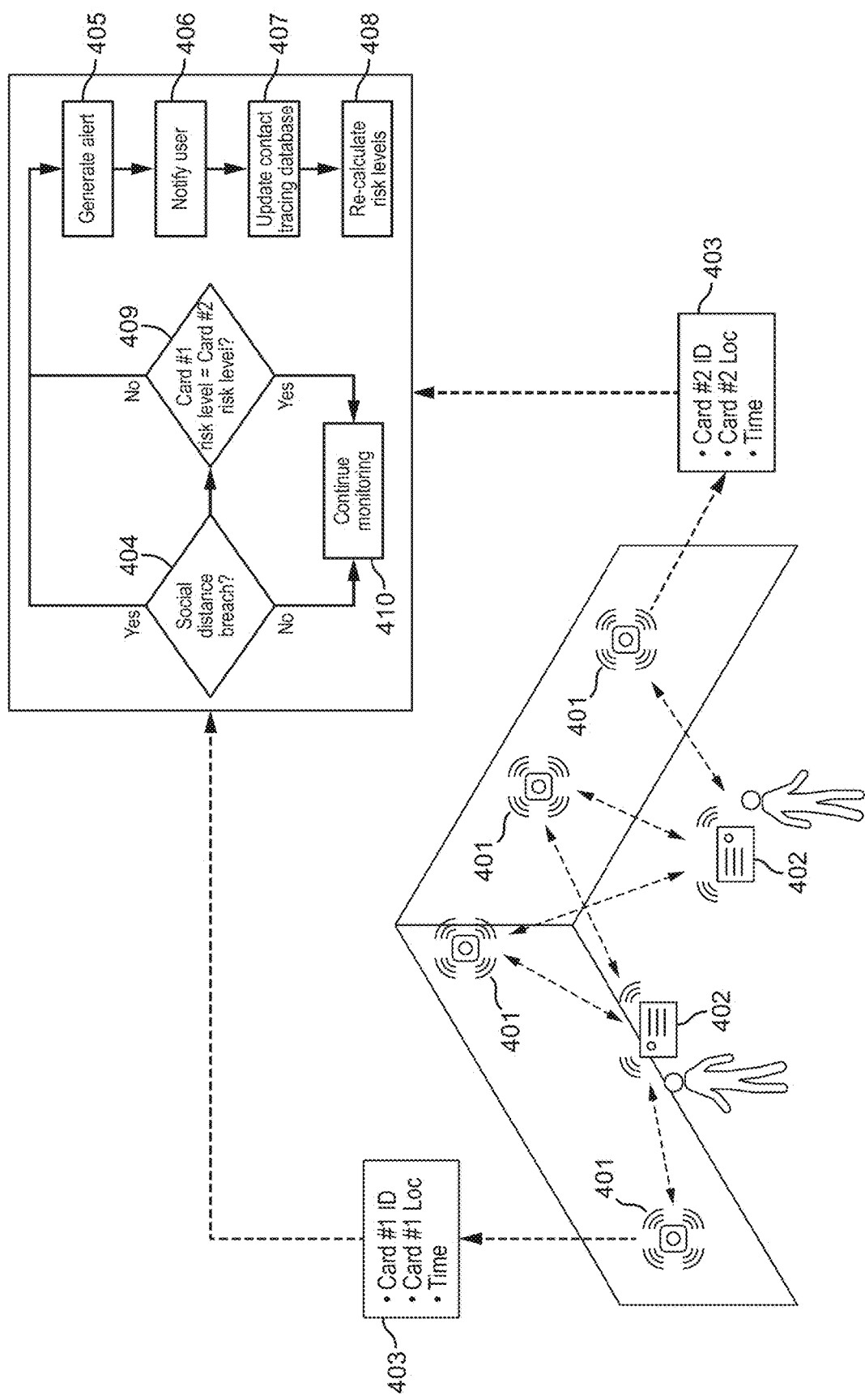
FIG. 4 is a diagram showing an implementing system for detecting person-to-person contacts, according to some embodiments.

Referring now to FIG. 4, a plurality of stationary transceivers 401 installed within a monitored area detect the location of a plurality of beacons 402 worn by persons occupying the monitored area. In some embodiments, the plurality of beacons include Bluetooth Low Energy (BLE) badges, Ultra-wideband (UWB) badges, or badges using a radio communications technology with an accuracy suitable for indoor location tracking. In some embodiments, the plurality of stationary transceivers include transceivers using a communications technology corresponding to that of the plurality of beacons. Tracking positions of the plurality of beacons may include, for each beacon, detecting, by each of three or more transceivers, a distance between the transceiver and the beacon and performing a triangulation calculation based on the distances and the positions of the transceivers to determine a position of the beacon. When beacon 402 is within range of transceiver 401, it transmits information 403 including its beacon identifier, the identifier of any beacon that has come within its contact range (as defined by system 100), and time data. Information 403 may be analyzed to determine whether a social distance breach has occurred 404. In the event of a social distance breach, the system generates an alert 405, notifies the user 406, updates a contact tracing database 407, and may re-calculate a risk level for the respective beacons 408, relating to the risk level assigned to particular occupants or class of occupants. If a comparison of the risk levels of two beacons leads to a determination that they are of different risk levels 409, alert 405, notification 406, database update 407, and risk level re-calculation 408 may occur. Where no social distance breach has occurred and there is no difference in risk levels, the system continues monitoring 410.

Figure 5:
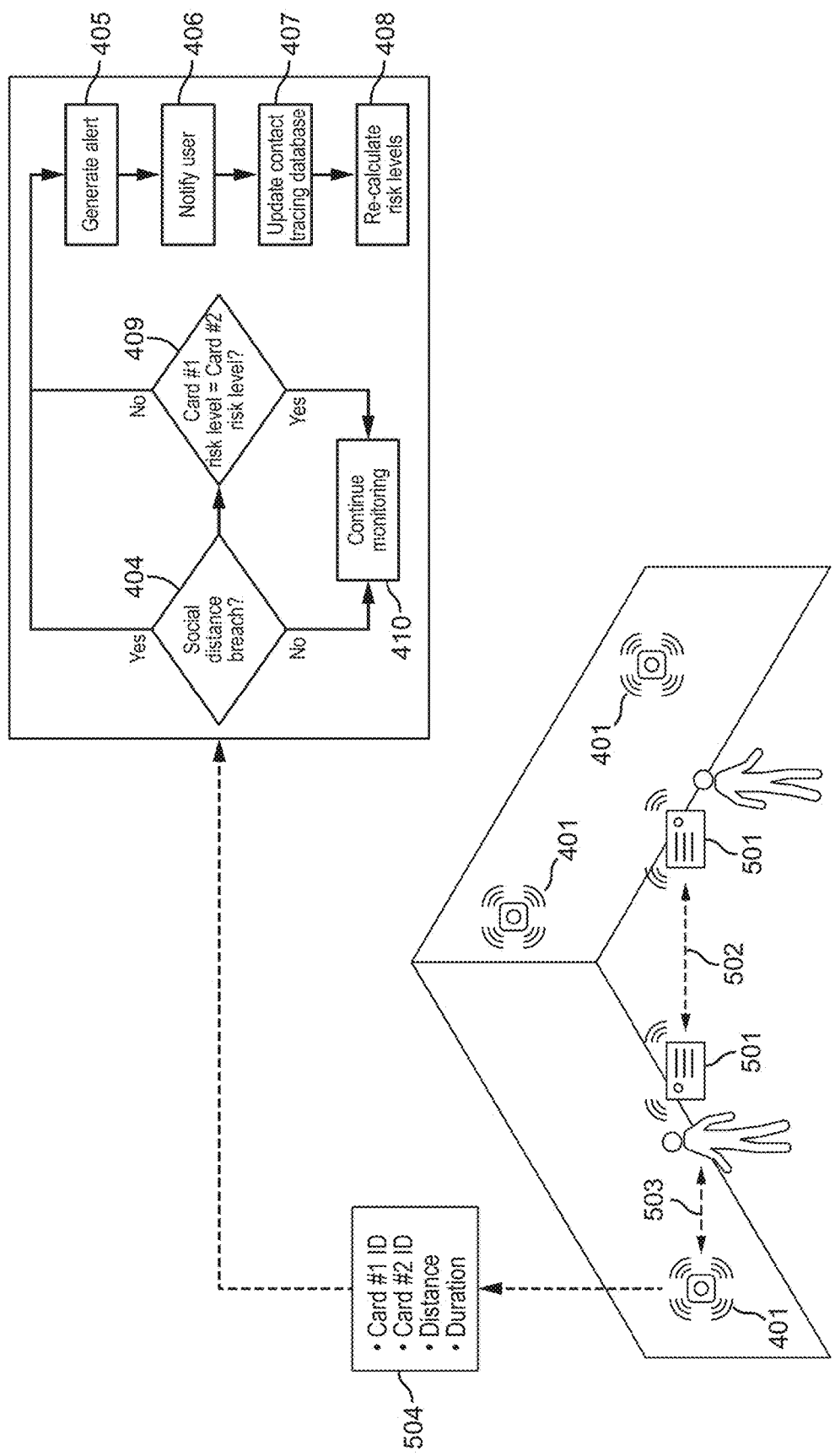
FIG. 5 is a diagram showing another implementing system for detecting person-to-person contacts, according to some embodiments.

Referring now to FIG. 5, an alternative embodiment of the method of FIG. 4, based on communications between badge transceivers 501 carried or worn by persons occupying the monitored area. In this embodiment, badge transceivers 501 are Bluetooth Low Energy (BLE) transceivers, Ultra-wideband (UWB) transceivers, or other badge transceivers using a radio communications technology with an accuracy suitable for indoor location tracking. Badge transceivers additionally include processing circuitry, memory, storage, and computer-readable instructions that can be executed by the processing circuitry. In some embodiments, badge transceivers are not badges, but devices, such as mobile or wearable devices. A plurality of stationary transceivers 401 installed within a monitored area detect the location of the plurality of badge transceivers 501 worn by persons occupying the monitored area. Tracking positions of the plurality of badge transceivers may include, for each badge transceiver, detecting, by each of three or more stationary transceivers, a distance between the stationary transceiver and the badge transceiver and performing a trilateration or triangulation calculation based on the distances and the positions of the stationary transceivers to determine a position of the badge transceiver.

In some embodiments, each badge transceiver transmits its identification data and location and each location is timestamped and saved by the badge transceiver 502. In other embodiments, the badge transceiver only records its location and location timestamp upon detecting another badge transceiver. Badge transceiver receives transmissions from other badge transceivers within range. Upon detecting another badge transceiver, badge transceiver receives the other badge transceiver's location with timestamp. The transceivers collect the badge transceiver identification data, badge transceiver location, and time of location and transmit this information to a remote infection risk management system.

In other embodiments, badge transceiver only calculates the distances between itself and other detected badge transceivers and the timestamps of each distance measurement and then transmits this information to the nearest stationary transceiver for onward communication to and processing by the infection risk management system. In some embodiments, badge transceiver detects a distance between itself and another badge transceiver that meets a rule distance criterion and badge transceiver records the time the criterion was met. Badge transceiver continues to calculate its distance from the other badge transceiver and, upon detecting that the distance criterion is no longer met, records the time that the criterion is no longer met. Badge transceiver may either calculate that the time duration meets the time criterion or may simply send the duration of the record of the distance criterion being met to the infection risk management system. In some embodiments, each badge transceiver sends this information to the nearest stationary transceiver as soon as it is within range 503. In some embodiments, badge transceivers may send this information to other badge transceivers within range. Information 504 sent to the infection risk management system may be analyzed in a similar manner to that described above in relation to FIG. 4.

In other embodiments, badge transceivers may be equipped with Near-Field Magnetic Induction (NFMI) communication technology configured to generate short-range magnetic fields and detect the presence of other such NFMI-enabled badge transceivers within the range of such magnetic fields. In such an embodiment, the short range of NFMI (approximately 2 meters) allows the system to be configured such that a straightforward detection of another card could raise an alert in the system of a contact between persons that breaches a social distancing guideline, or that may create a change in the risk levels of the occupants to which the badge transceivers are associated. A communication with the infection transmission risk manager, and a similar analysis of the nature of contact and the impact on risk levels, may occur upon such a detection, in a manner similar to that described above and in relation to FIG. 4.

Figure 6:
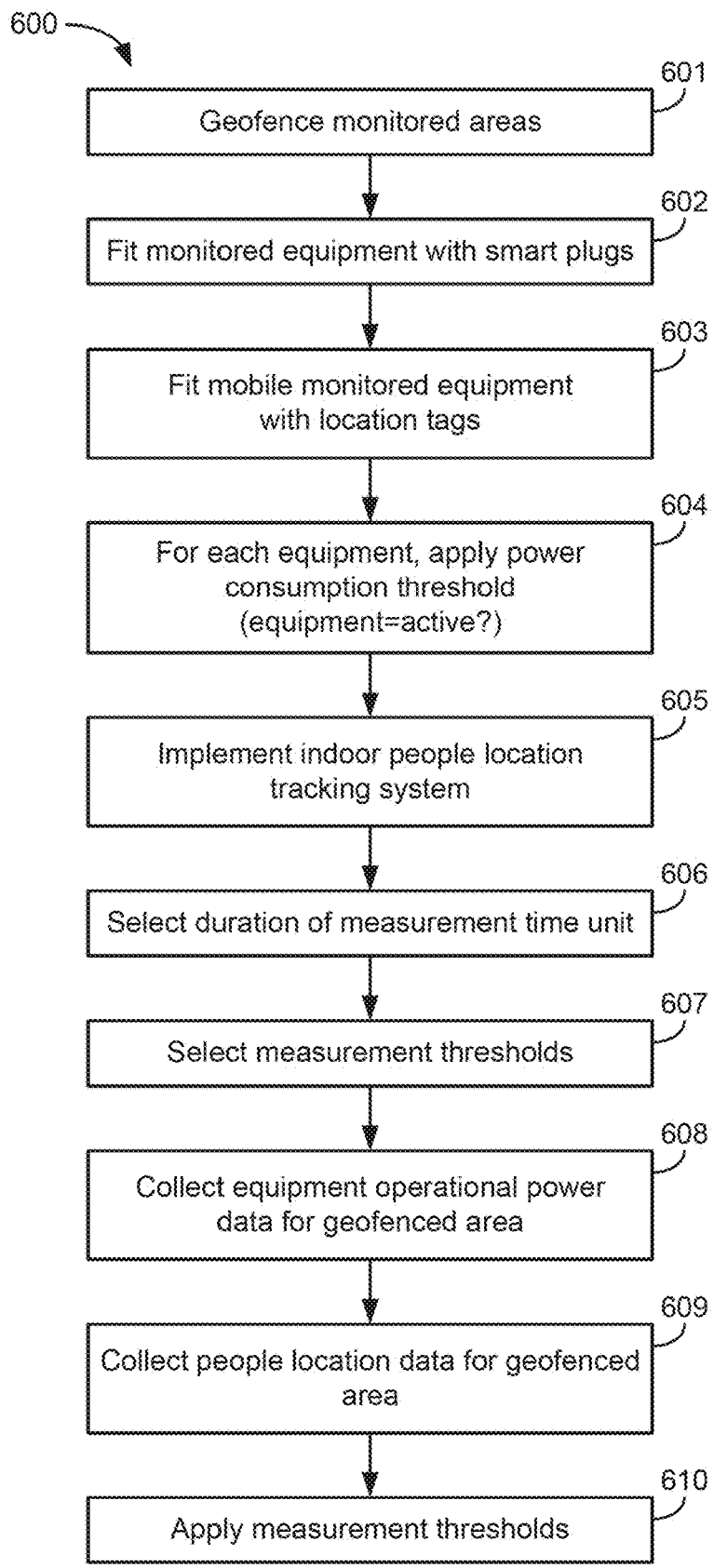
FIG. 6 is a flowchart of a method of configuring the system and recording various data, according to some embodiments.

Referring now to FIG. 6, a flowchart describing a process of configuring a system and recording data. At step 601, monitored areas (spaces) are geofenced. For example, the boundaries of the spaces may be virtually defined within system 100 to denote the geographic limits of each space. In some cases, each space is differentiated by a wall or other physical structure. In other cases, two or more spaces may be open or continuous but defined as separate spaces using a geofencing approach at step 601.

At step 602, equipment 104 is fit with smart plugs 103A. For example, each device of equipment 102 may be associated with a particular smart plug 103A attached to a power cord of the device. Step 602 may include configuring the infection transmission risk manager 101 to map each smart plug 103A (and the data provided thereby) to a particular device of equipment and/or to a type of equipment.

At step 603, mobile/movable devices of equipment 102 (i.e., devices that are configured to be moved to various spaces of the laboratory over time) are fit with location tags (e.g., trackable beacons). Step 603 may include configuring the infection transmission risk manager 101 to associate each location tag with the corresponding equipment 102, i.e., such that the infection transmission risk manager 101 can determine which equipment 102 is present in a space based on tracking data from a particular location tag.

At step 604, a power consumption threshold is defined for each device of equipment 102. For example, the infection transmission risk manager 101 may store a set of power consumption thresholds (e.g., values of amounts or rates of power consumption) for each type of equipment 102 or for each particular device of equipment 102. Step 604 may include mapping each device of equipment (and, in concert with step 602, each smart plug) with a power consumption threshold. The power consumption thresholds can be determined experimentally and/or input by a user, or may be determined using machine learning methods.

At step 605, the occupant tracking system 104 is installed and configured. For example, the occupant tracking system 104 may be configured to coordinate with the geofenced borders defined at step 601, i.e., such that the occupant tracking system 104 is configured to provide data relating to which geofenced space an occupant is located in. In some embodiments, step 605 includes configuring the occupant tracking system 104 and/or the infection transmission risk manager 101 to associate each of multiple occupant beacons with a particular user and/or a type of user (e.g., based on role, job title, etc.).

At step 606, the duration of measurement time units is selected. For example, as described above, the equipment and occupancy utilization can be calculated based on a discretized set of sub-periods (measurement time unit), the length of which can be selected at step 606. Step 606 thereby allows tailoring of the temporal resolution of the utilization logging described herein.

At step 607, measurement thresholds and parameters are set. The measurement thresholds and parameters may include minimum dwell times for an occupant to be counted as occupying a space. The measure thresholds and parameters may also include assumed (automatically added) equipment set-up, start-up, shut-down, or cleaning times. In some embodiments, the measurement thresholds and parameters include expected or maximum occupancy values, weighting factors, or other terms that customize the utilization calculations based on the type of space being evaluated.

At step 608, power consumption data for equipment in a space (e.g., within a geofenced boundary) is collected. For example, the power consumption data may be measured by the smart plugs 103A and transmitted to the infection transmission risk manager 101 via a wireless network. The power consumption data may be stored by the infection transmission risk manager 101 for later use in identifying possible incidents of infection transmission.

At step 609, occupancy data is collected for the geofenced space. For example, the occupant tracking system 104 may provide data relating to the positions of tracked personnel in the space (e.g., the determined locations of tracked beacons in the space). The occupancy data may include timing information describing when an occupant entered or left a space. The occupancy data may be stored by the infection transmission risk manager 101 for later use in identifying possible incidents of infection transmission.

At step 610, measurement thresholds are applied. For example, at step 610 the infection transmission risk manager 101 may remove occupancy data that indicates an occupant present in a space for less than the minimum dwell threshold. As another example, at step 610 the infection transmission risk manager 101 may determine the statuses of the equipment 102 over time by comparing the power consumption data to the power consumption threshold(s) for the equipment 10. Applying the measurement thresholds 610 may thereby result in a set of occupancy data that defines a number of occupants at a space for each of multiple sub-periods and a number of active devices of equipment for each of the multiple sub-periods.

Social Distancing Occupancy Alerts

One implementation of the present disclosure is a process for detecting an unsafe number of people in an area, in breach of minimum social distancing advice, according to some embodiments. If too many people enter the room it should trigger an alert and an SMS or other notification should be sent to all people that entered. The alert may appear as a notification on a UI dashboard, as a push notification to a mobile device, as a visual or auditory alert within the room, or some other method.

The rule for the required distance between people may be hard-coded, entered by the user as a numerical value, derived from a user's selection of a known contagion, automatically updated through calls to a remote service, or set through some other method. In some embodiments, the system applies multiple different rules in parallel, representing different parallel contagions, different models of the same contagion, or for some other purpose.

In some embodiments, the social distancing monitoring system is configured with a rule specifying the maximum number of occupants within a defined space, such as a room. The maximum number of occupants may be set manually for each space or may be determined through calculation. For example, the area of the room may be manually provided, or calculated from the geofence definition, and then divided by the area of required space around an individual occupant. In some embodiments, the system utilizes an algorithm to pack circles, representing the required social distancing area around an individual, into the geometry of the room, and the maximum occupancy is the maximum number of non-overlapping circles that fit into the space. The tracking of occupancy may be performed by defining geofenced regions, and then tracking individuals entering and leaving those regions.

In some embodiments, the social distancing monitoring system is configured with a rule specifying criteria for a maximum distance between two beacons and a maximum time period during for the distance between two beacons being shorter than the maximum distance. Where the system detects that the time and distance criteria of the rule are met in respect of two beacons, the system generates an alert to the user (e.g., by sending a notification to a cellphone associated with that user's beacon). A social distance rule breach alert is raised and sent to a monitoring client and a contact tracing database is updated.

Badge transceiver may contain instructions including a social distancing rule specifying distance and/or time criteria that, if met, cause badge transceiver to generate a social distancing breach alert. In some embodiments, badge transceivers may transmit rule breach information for other badge transceivers to the nearest stationary transceiver within range. In some embodiments, the determination that a social distancing guideline has been breached is made by the badge transceiver. In other embodiments, this determination is made by the system, using distance calculation data and time data provided by a badge transceiver. In some embodiments, a determination that a social distancing guideline has been breached causes the system to generate an alert to the user (e.g., by sending a notification to a cellphone associated with that user's badge transceiver). A social distance rule breach alert is raised and sent to a monitoring client and a contact tracing database is updated.

In some embodiments, proximity detection alerting and contact tracing database updating may relate to a designation of an individual card holder as being a 'High Risk' individual, based on confirmation that the person has a positive diagnosis of an infectious disease.

In some embodiments, an occupancy for a monitored space may be determined using methods that do not require a person to have a badge or beacon, for example through the active or passive interaction of people with people-counting sensors (e.g., camera sensors, infra-red sensors, etc.) and other devices of an access control system, such as request-to-entry (REX) devices and other access control infrastructure indicating entry into or exit from a space. The people counting data from such systems may be analyzed by the infection transmission risk manager to determine whether a maximum safe occupancy of a monitored space has been exceeded or is close to being exceeded and generate an alert to the system, occupant notification, and event logging for reporting and further analysis.

Occupants, Spaces, and Equipment with Varying Degrees of Risk

Figure 7:
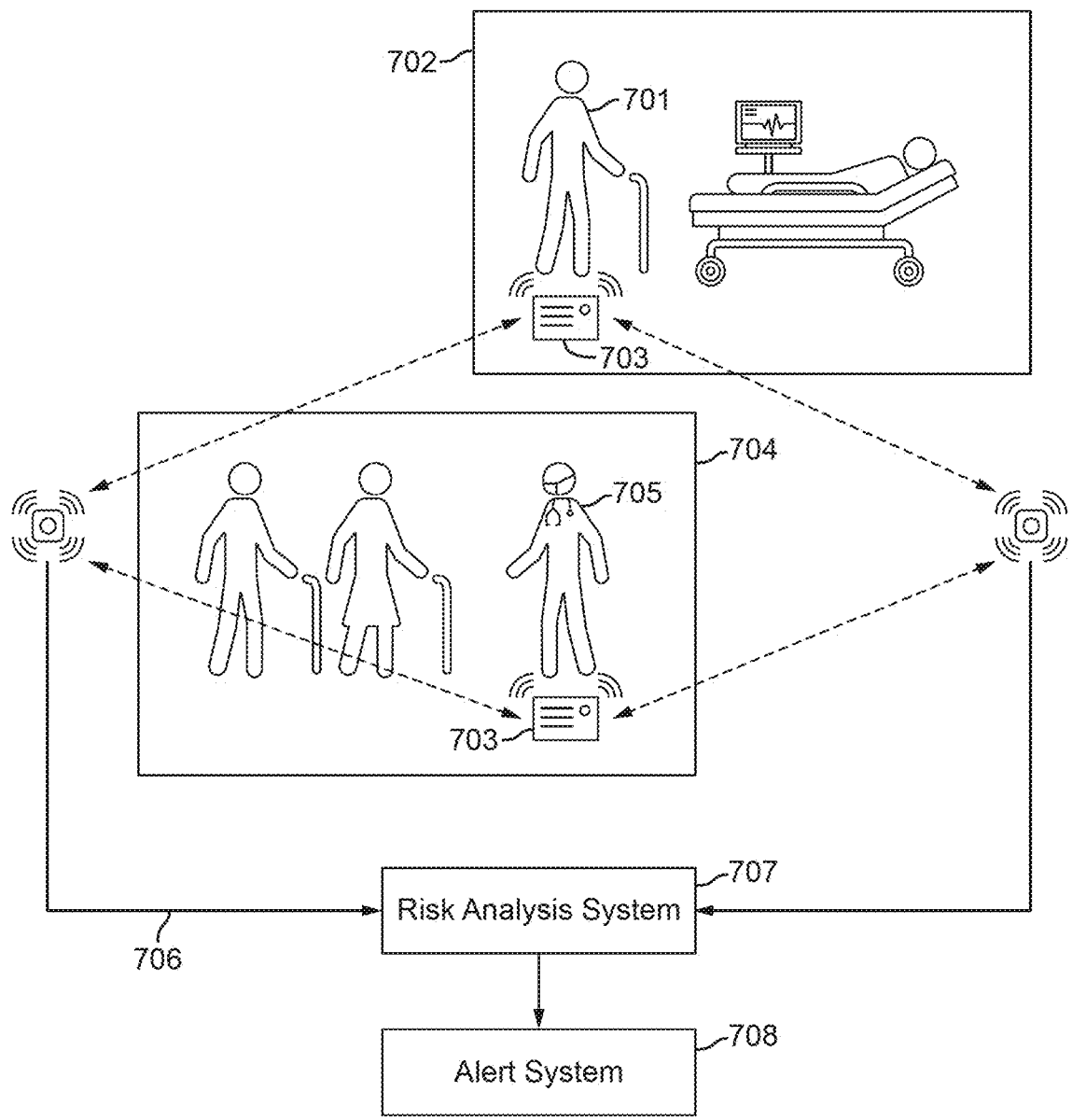
FIG. 7 is a diagram showing a process for detecting high risk individuals accessing monitored areas, according to some embodiments.

FIG. 7 describes a process for a method of detecting high risk employees or other personnel accessing safe areas or otherwise changing a risk rating of an area or the people using the area. ID cards 703 associated with individual users 701 and 705 may be given a risk rating, based on a role of a user (e.g., a person whose role brings them into contact with many new individuals) or an attribute of a user (e.g., user has been confirmed as testing positive for an infectious disease). Alternatively, a user may be identified in the system as an 'At Risk' user (e.g., a user with a particular risk factor for a current epidemic, such as their age or having a relevant pre-existing medical condition). A risk analysis system 707 that may form part of infection transmission risk management system 101 receives location tracking data 706 of persons 705 with, e.g., a 'High Risk' rating and an alert 708 may be raised if the high risk user enters into an area geofence designated an 'At Risk' area 704 or an area otherwise required to be maintained at a low level of risk for contamination. In an alternative embodiment, the system may additionally designate an "At Risk" user group 701 and those users monitored to ensure they do not enter into a 'High Risk' area 702 for contamination.

The system may additionally identify a risk rating for persons at low risk of contamination and notify users of their low risk. A person may be identified as low risk due to the person's role or an attribute of the person, such as immunity from past infection. In particular, for contagions to which adult populations are known to have a high percentage of immunity, such as Chicken Pox, identifying low risk individuals may enable organizations to continue to operate with minimal disruption.

The risk analysis system may use data about the proximity of individual users with different risk ratings to create new risk ratings for users. For example, a high risk individual may come into contact with a low risk individual, leading to a re-classification of the low risk individual as one of a medium risk group. Additionally, individual user notifications could be sent to users to notify of a risky contact. A contact tracing database may be updated with these interactions, and an alert may be sent to a monitoring client application.

The system may additionally record the identities of individuals with a high transmission risk rating, the identities of individuals they were in close contact with (as defined by the system), and the duration and location of the interaction. The monitoring system may generate a prioritized list of persons that were most likely to have been exposed to an infectious disease from direct interaction with a person with a confirmed diagnosis. In addition, the monitoring system may create a report specifying the identities of individuals that did not have direct interaction with the infected person, but who used an area used by the infected person within a defined time period. Similarly, the monitoring system may generate another prioritized list of persons that were most likely to have been exposed to an infectious disease from contact with contaminated surfaces or airborne contamination from a known infected person, based on a determination that they shared the same space (identified by a person's presence within a geofence) within a definable time window (based on infection data, such as infection transmission dynamics and survival duration on surfaces or in the air). The monitoring system may, additionally identify locations where a person with a positive diagnosis spent significant periods of time and the system may update its risk ratings for different areas and, where relevant, any equipment therein, based on this information.

The system may additionally re-calculate risk levels, depending on different factors. For example, a risk level for a person may increase after a detected contact with a higher risk person, equipment, or space. Conversely, a risk factor for a person, equipment, or space may decrease following a recorded completion of a cleaning operation. In some instances, the change in risk factor may depend on a time window before or after a risk-altering event. For example, after high risk contact occurs for a person, the system may record that person performing a hygiene operation within a configurable time window. The risk factor for that person may initially have increased, but is then decreased due to the completion of the sanitation operation within the required time.

Asset Tracking

Figure 8:
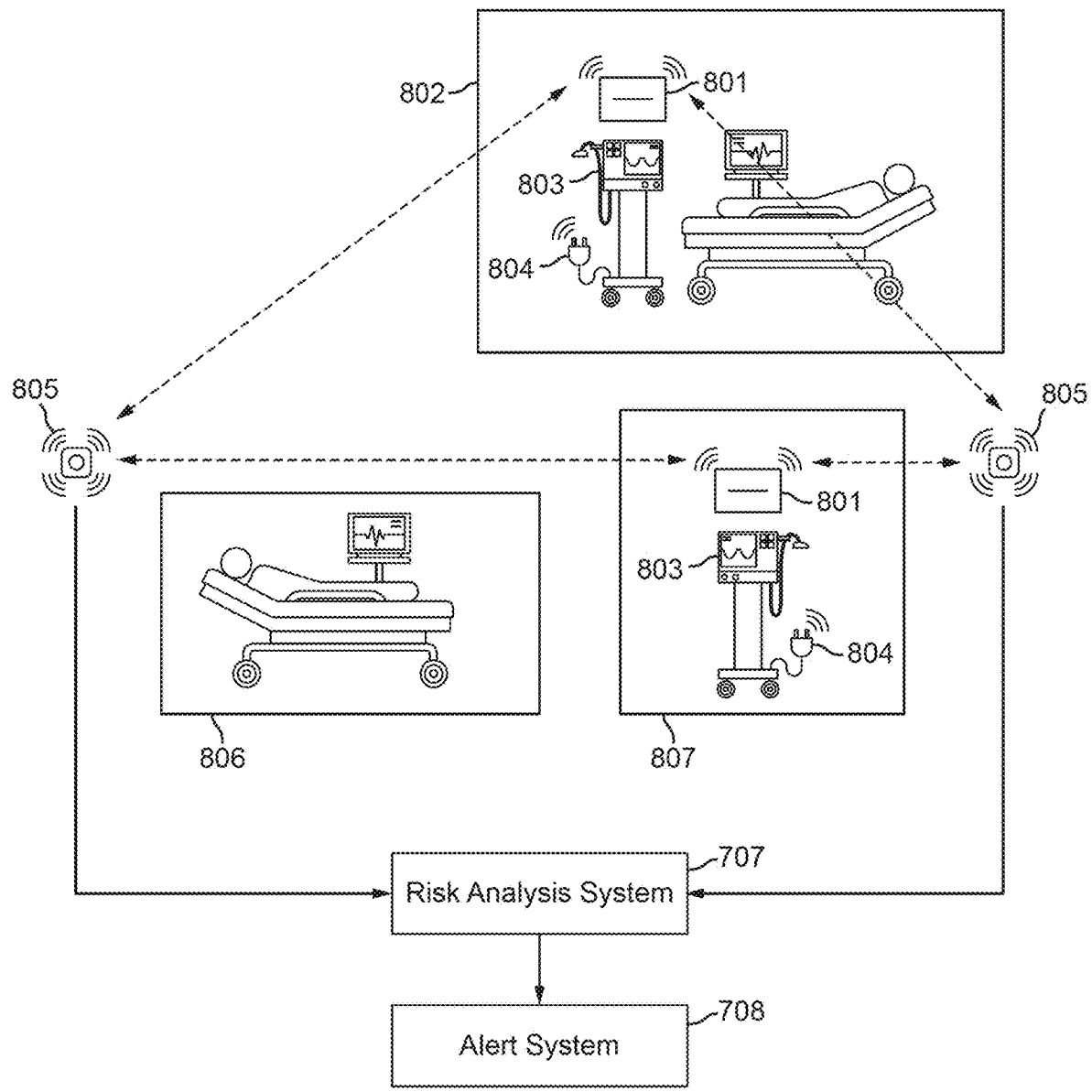
FIG. 8 is a diagram showing a process for monitoring critical mobile assets, according to some embodiments.

FIG. 8 describes a system for monitoring a critical mobile asset (e.g., a ventilator in a hospital) and a means of identifying the asset's availability and a risk assessment of that mobile asset, based on usage and location data for the asset. Usage data may include sensor data indicating interaction of a person with the asset or may include a power consumption 804 data about the asset, indicating that the asset is or has been in use. Mobile asset's 803 location tag 801 communicates with stationary transceivers 805 that record the asset's location. Asset's location may fall within a geofence of an area that has been indicated in the system as being a high risk area for contamination 802. For example, a geofence may be defined within an ad hoc medical facility, such as a field hospital, for dealing with an epidemic and relating to a triage area or a high-traffic area where contamination risk is higher. Alternatively, a geofence may define an area for a critical asset within which the asset must remain 806, and the system may generate an alert 808 upon the asset being detected at a location outside the geofence 807 or, alternatively, the asset's location not being detected within the required geofence. A change to such asset's risk level may be recorded in the system.

Contact Tracing

One implementation of the present disclosure is a method of retrospectively reviewing contact log information to identify potential transmission or contamination caused by an individual, where that individual has been identified as being infected by a contagion.

In some embodiments, the system can be supplied with the ID of a specific target individual, and a time window. The system then processes log data to identify the spaces, equipment, and other individuals that the target individual came into proximity with, during the set time window. In some embodiments the length of time that the target individual was in proximity to another individual, piece of equipment, or within a space is taken into consideration. Extended periods of proximity may be used to increase a determined risk that infectious transmission or contamination has taken place.

Information relating to the presence of an infected person within a space and the duration of presence may additionally be used by the monitoring system to initiate a targeted decontamination of the relevant areas and equipment, rather than decontaminating a wider area.

In some embodiments, low risk users may be eliminated from an infection risk analysis or a contact tracing history, for a more accurate picture of transmission and a more effective management of social distancing rules, with lower business impact. The system may additionally identify equipment used by an infected person, based on person's location data in respect of location data and/or sensor data of the equipment (e.g., correlating person location with mapped location of equipment, equipment beacon location data, power consumption data indicating equipment is in active use, sensor data indicating interaction of user with equipment, such as opening a refrigeration unit door). The system may use this data to create a prioritized list of equipment that is most likely to have been contaminated by an infected person.

Figure 9:
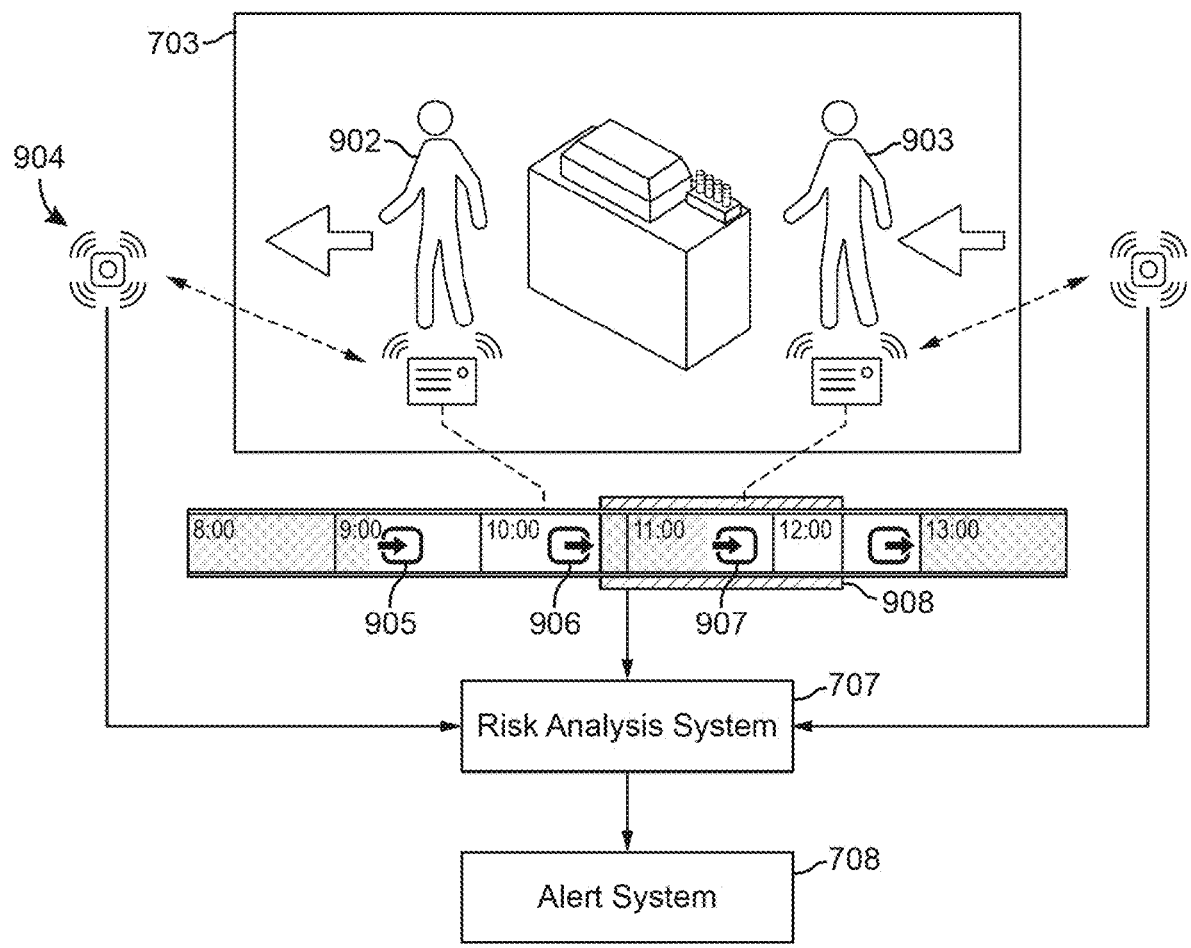
FIG. 9 is a diagram showing a process for detecting a risk of human to surface contamination, according to some embodiments.

FIG. 9 describes a process for detecting a risk of human-to-surface contamination and onward human transmission, using people tracking data, room geofences, and equipment usage monitoring. For example, a person 902 uses a small room for a minimum time period (e.g., more than 15 minutes/1 hour etc.). That person 902 is detected by sensors 904 of occupant tracking system 104 within room geofence 901, and the start time 905 and end time 906 of that presence is recorded. In the same example, a subsequent detection of other persons 903 is made in the same location 901 and that presence is detected to occur 907 within an unsafe time window 908 for contamination risk. Such space and time overlap analyses may be made in respect of desks, laboratories, conference rooms, meeting rooms, or in any shared space whose location or geofence is defined in the system. User risk ratings may change, based on the analysis. Space and associated equipment risk ratings may change, based on the analysis.

Recording Cleaning Events

Figure 10:
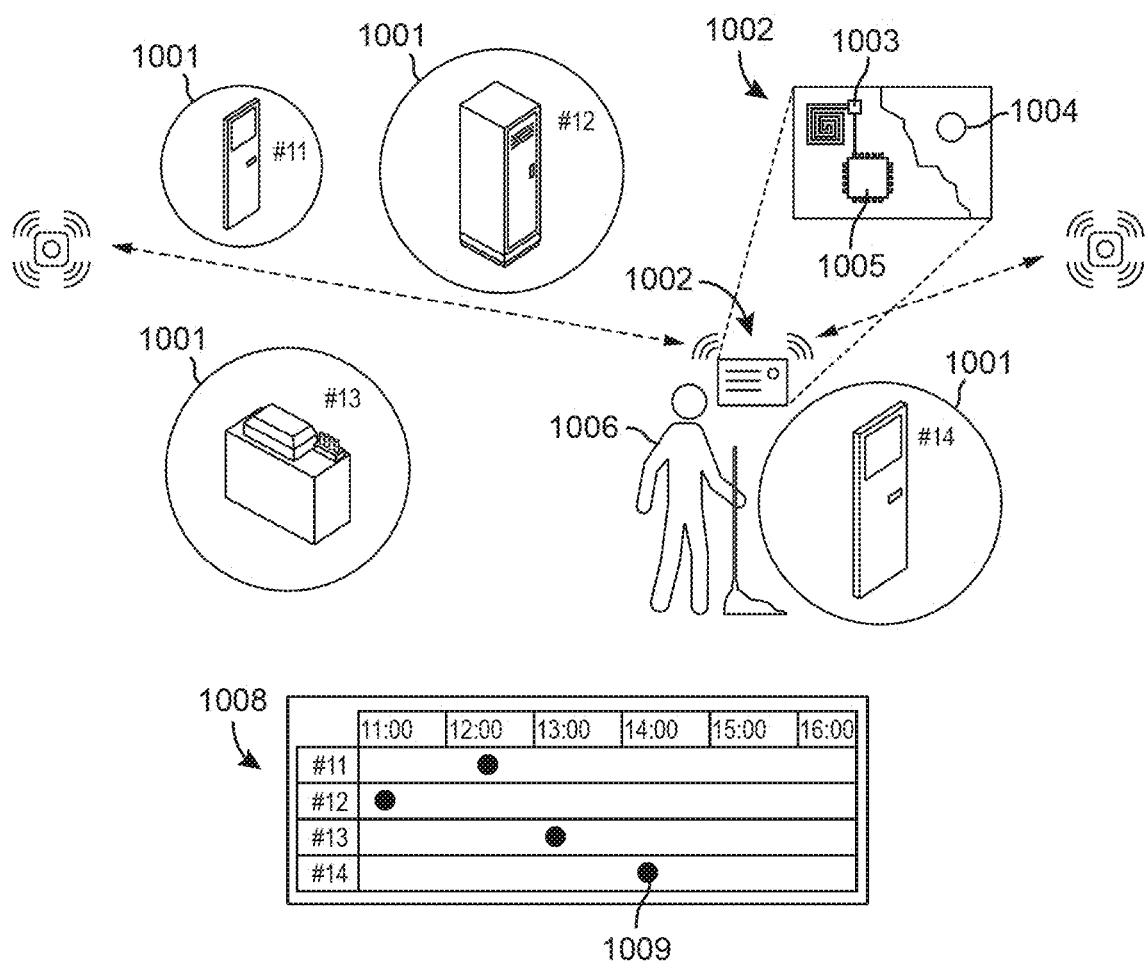
FIG. 10 is a diagram showing a method of recording cleansing operations on a target surface, according to some embodiments.

FIG. 10 describes a method of recording completion of a cleansing operation on a target surface, e.g., a door handle, door plate, equipment, or other surface, in accordance with a cleaning schedule. A special purpose transceiving card 1002 comprises a button 1004, which enables a janitor or cleaner 1006 to confirm completion of a cleansing operation. In some embodiments, the button is connected to a microprocessor 1005 and wireless communication circuitry 1003. Pressing the button triggers the microprocessor to transmit the card's location to the central system 1008. In such an embodiment, the locations of specific surfaces or general areas 1001 to be cleaned are mapped in system. When the system receives communication from the transceiving card, the system determines the nearest mapped cleaning location 1007 to the current location of the transceiving card, and then associates a cleaning event 1009 with that mapped cleaning location.

In some embodiments, the transceiving card comprises a plurality of buttons, each of which may have a specific purpose. For example, buttons may be provided to indicate that a nearby door needs cleaning, that the door has been cleaned, or that a hand sanitizer dispenser requires refilling. In some embodiments, to reduce the risk of transferring contagion between a cleaning operative's hand and the transceiving card, the button may be replaced by optical or ultrasonic sensors to detect hand gestures, be automatically triggered by dwell time, or use some other method.

In some embodiments, the logged event of a cleaning operation reduces the risk rating of an area or piece of equipment. In some embodiments, the logged event of a cleaning operation is taken into consideration in the contact tracing process. If a cleaning operation is logged in an area that was previously used by an individual that is a contagion risk, then the risk is reduced for any individuals that use the area after the cleaning operation. However, the cleaning operative themselves may still be determined to be at high risk from the contagion.

Alternatively, the signal from the transceiving card, triggered by the press of a button or other method, may indicate that an area requires cleaning. For example, an individual may recognize that they have not adequately contained a sneeze or a cough, and then use their transceiver badge to request that an area be cleaned. The system may also be used to report events such as spillages.

Hand Hygiene Monitoring and Sanitation Consumables Monitoring

In some embodiments, a hygiene and sanitation support system may ingest data from connected hand sanitizer dispensers. Said hand sanitizer dispensers may comprise a sensor to determine remaining levels of hand sanitizer, microprocessor, and wireless communication circuitry. If a hand sanitizer dispenser senses that it is empty, then it may communicate that status to a central system. A user interface may then show the location of hand sanitizer dispensers that require filling on a system map view and an SMS or other notification may be sent to an appropriate individual. Additionally, person tracking system may be used to determine the nearest janitor or cleaner in the vicinity of a dispenser requiring refilling and an alert may be sent to that person's cellphone.

In some embodiments, a user may be able to manually request that a hand sanitizer dispenser be refilled. In embodiments where users carry a transceiving card, and where that card can be activated to send a cleaning request, the triggering of such a cleaning request while in close proximity with a hand sanitizer dispenser may be interpreted as a request to refill said hand sanitizer dispenser.

In some embodiments, a social distancing analysis system may ingest data from connected hygiene monitoring equipment and update the risk rating of a user based on a determination for a user of a failure to comply with correct hygiene procedures. The hygiene equipment may be a hand sanitizer dispenser, where the procedure may simply be use of the equipment. The hygiene equipment may be a hand hygiene monitoring sensor, where the procedure may relate to appropriate duration and/or motions for hand washing. In some embodiments, the system may send an SMS notification when a card passes some area without triggering the required hygiene equipment.

User Interface Output

A user interface for the outputs of the disclosed systems and methods may include various embodiments, such as a map or floorplan of the monitored area overlaid with geofenced boundaries of individual spaces, the mapped locations of stationary equipment or current locations of mobile equipment, the locations of people or events, which may be indicated by icons, heatmaps, etc. A user interface may display indications of contamination hotspots, risk ratings for people, equipment, or spaces, or infected person trails, with time and risk information. Alerts may displayed for equipment in a high risk area or cleaning alerts.

Simulating the Spread of Contagions

One implementation of the present disclosure is a method to simulate the spread of a contagion based on historical data, live data, or predicted data.

In some embodiments, simulating the spread of contagion using historical data shares some of the features described for running contact tracing reports. Parameters can be adjusted for each simulation, such as the percentage chance of transmission, how the chance of transmission increases as the length of exposure time increases, the incubation period, the period of communicability, and at what stage the individual may stop attending work due to the illness. One or more individuals may be selected as the source of the contagion. The potential spread of the contagion can then be simulated based on the historical data of person-to-person interactions, potential person-to-surface to person transmissions, cleaning events, and any other relevant recorded data. Additional events may be interjected during the simulation, such as selecting another individual to be a source of contagion, adding cleaning events, and simulating sending an employee home by ignoring their interactions after a set point in time.

In some embodiments, simulating the spread of contagion is run on predicted data. Machine learning models may be trained on historical data, and then used to simulate the behavior of occupants. This enables interventions that were not present in the historical data, such as restricting the spaces that certain occupants can visit and reducing maximum occupancy limits for rooms.

In some embodiments, simulating the spread of contagion is run in real-time. Parameters can be adjusted in advance of or during the simulation, as described for running simulations on historical data. The potential spread of the contagion is then simulated based on the live data of person-to-person interactions, potential person-to-surface to person transmissions, cleaning events, and any other relevant data. In a live simulation, the effect of interventions such as reducing maximum occupancy limits for rooms and providing guidance to occupants can be observed, rather than a simulated ideal. For example, occupants may not follow guidelines or there may be unexpected consequences, such as restrictions in one area leading to increased occupancy in other areas.

Reports may be run on the results of simulations or on historical data to identify individuals that had the most person-to-person contacts within a given time window, individuals that visited the largest number of separate locations, or to identify other information that is useful in anticipating the spread of a contagion.

Dynamic Workspace Reservation

Overview

Figure 11:
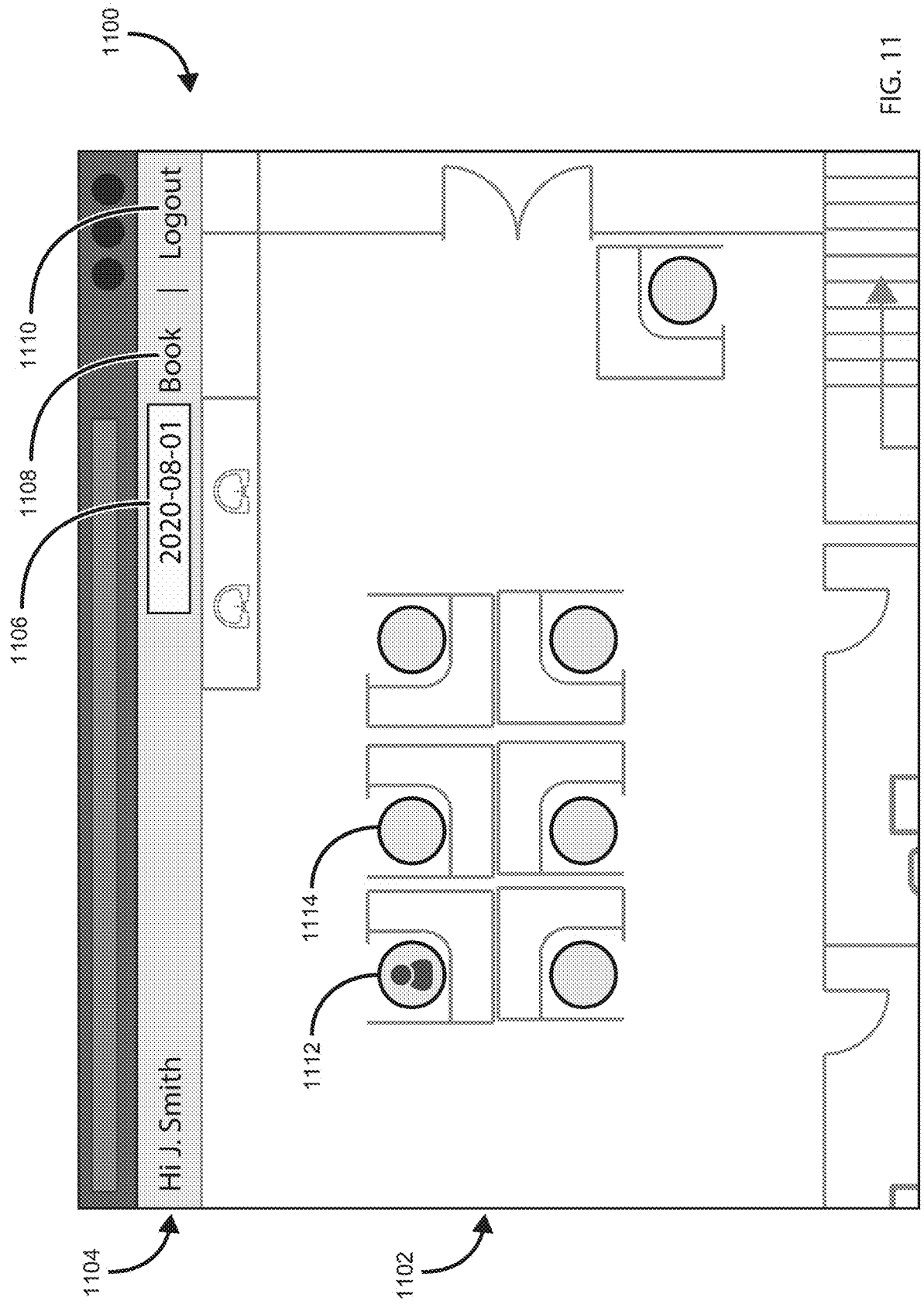
FIG. 11 is a diagram of a user interface for reserving workplace stations, according to some embodiments.

Referring now to FIG. 11, user interface 1100 for facilitating reservations for workplace stations is shown, according to some embodiments. Interface 1100 may be implemented on any of a variety of different user devices (e.g., smartphones, tablets, workstations, laptops, home computers, etc.) and may entirely store applications displayed on interface 1100, or host applications displayed on interface 1100 that are stored elsewhere. Interface 1100 is shown to include application 1102.

Application 1102 may be configured to receive user requests for reserving workplace stations and update interface 1100 based on user requests—for the user and/or other users of application 1102—accordingly. In some embodiments, application 1102 is stored on premise (e.g., on a server within the building in which the user is using the application 1102). In other embodiments, application 1102 is stored at a data center off-premise (e.g., on a server at a location other than the workplace building, on a server at a location other than the user, etc.) and accessed via a cloud network. Application 1102 may include various widgets and/or functionalities, including menu bar 1104, date button 1106, book button 1108, logout button 1110, workplace station 1112, and workplace station 1114. Various examples of a user using application 1102 to book a workplace station are described below.

For example, a user wishes to reserve a place to work (e.g., workplace station, etc.) upon entering a workplace building. Social distancing laws, regulations, and/or rules may be implemented that prevent typical workplace locations for workers within the building (e.g., two workers cannot sit next to each other if their desks are proximate within six feet). Social distancing, as referred to herein, may include the practice of increasing the space between individuals and/or decreasing the frequency of contact to reduce the risk of spreading a disease (e.g., COVID-19, etc.). These practices may include maintaining at least a threshold distance (e.g., 6 feet) between all individuals, in some instances even those individuals who are asymptomatic. Social distancing strategies may be applied on an individual level (e.g., avoiding physical contact, etc.), a group level (e.g., canceling group activities where individuals will be in close contact, etc.), and/or on an operational level (e.g., rearranging chairs in a dining hall to increase distance between them, etc.). In some embodiments, "pods" may be implemented in the workspace, such that a group of people may interact with each other to some extent (e.g., within the same room, etc.) but are isolated from other pods. The pods may decrease a level of risk associated with each workplace station. This is described in greater detail below with reference to FIG. 15.

In some embodiments, users may login to application 1102 via a profile, whereby user-specific information can be provided to application 1102 (e.g., user preferences, assigned seating preferences, etc.). Additionally, application 1102 may provide the assigned seating information and other information to the user based on their user profile. In some embodiments, application 1102 includes an icon that indicates their assigned location, a zoomable, scrollable map, or both, viewing may be based on their assigned seat, last booked seat, most common booked seat, future booking etc.

A user may engage date button 1106 and selects a date, which displays the workplace station window in application 1102. Workplace stations 1112, 1114 may be selected to reserve the office space for that day. The reservation may include a range of time (e.g., 1 hour, 1 day, 3 days, etc.). The reservation may only be limited to particular seats. For example, user John may only be able to reserve seating in workplace station 1112, while user Jane may only be able to reserve seating in workplace station 1114. In some embodiments, application 1102 may only allow the users to reserve a workplace station that conforms to the social distancing regulations. Various embodiments relating to this are described below with reference to FIG. 12.

In some embodiments, application 1102 may include a toggle between settings for determining whether workplace reservation are allowed. For example, the above example may include a "COVID-19" setting that implements social distancing rules and regulations to make reservation decisions. A user may be able to toggle from the "COVID-19" settings to "NORMAL," "LOW-RISK," "FLU SEASON," or various other settings. These different settings may change the requirements for reserving workplace stations in application 1102.

While not shown in FIGS. 11-16, the level of risk and/or hazardous conditions may be displayed in application 1102. In some embodiments, this includes indications for varying levels of safety for the occupant(s), varying levels of hazardous conditions for the occupant(s), or a combination of both. The varying levels of risk and/or hazardous conditions can be provided to a graphical user interface (i.e., application 1102). In one example, this is done so a user of application 1102 can determine why their workspace station is not reservable, and which safety measures need to be implemented before the workspace is reservable.

In some embodiments, color-coded indicators can be used to display information relating to the workplace stations on application 1102. In one embodiment, a green-colored workplace station indicates that the workplace station is reservable or that it almost reservable (e.g., the workplace station is currently being sanitized, the workplace station is close to completing a time period for which the workplace station is unreservable due to safety reasons, etc.). A yellow-colored workplace station may indicate that there is a greater amount of time to wait until the workplace station is reservable than the yellow-colored workplace station, and a red-colored workplace station may indicate that there is a significantly more amount of time to wait until the workplace station is reservable (e.g., the workplace station just became unreservable, etc.).

For example, a yellow-colored workplace station symbol that represents a workplace station requiring hazardous may indicate that a risk score or level associated with the workplace station is below a threshold level, or that a restriction on the station is near being released (e.g., an amount of time before the end of a restriction period is less than a threshold amount of time). However, a red-colored workplace station may indicate that the workplace station has a risk score that is below a threshold level, or that a restriction on the station is scheduled to be in place for more than a threshold amount of time. Other methods for displaying gradations of hazardous workplace stations may also be considered.

In some embodiments, the gradations may be based on conditions inputted by managers of application 1102. For example, if risk levels are generally lower (e.g., in a particular geographic area, in a particular building or campus, etc.) with regards to a particular threat, such as an infectious disease, application 1102 may be programmed to show workplace stations that have been vacant for over a day in a low risk category. However, if risk levels are generally higher, application 1102 may be programmed to show only workplace stations that have been vacant for over three days in a low risk category. It should be appreciated that, in various implementations, any number of risk levels/categories could be shown, and they could be indicated in any manner, including, but not limited to, color, shading, stippling, or any other characteristics.

Application 1102 may further provide time indications for the users when workplace stations will become available. For example, a user may log on via application 1102 and see that there is still 10 minutes left for their assigned workplace station (via a visual timer) until they are able to reserve their station. Users of application 1102 may speed up the process by requesting a sanitization of their workplace station via a button on application 1102. In some embodiments, users receive a notification when their assigned workplace station is available for reservations.

In some embodiments, the timer can be color-coded to indicate how close the user is to being able to reserve a workplace station, as discussed below. For example, when a user logs into their profile and attempts to reserve a workplace station, they see a "green" timer indicating that they are almost able to reserve a workplace station, or a "red" timer indicating that they have a significant amount of time to wait to reserve a workplace station. The timer may begin at the end of the user's reservation period or as soon as their work shift is complete (e.g., when they leave the building). The icons (e.g., timer icons, etc.) may show a countdown to availability, or after being selected, an actual countdown or graphical representation could be shown.

While not shown in FIGS. 11-16, the location of workplace stations with respect to airflow paths may be considered by application 1102, according to some embodiments. For example, if a worker (e.g., user of application 1102) finished using their workplace station and the workplace station is now indicated as being potentially hazardous, and the workplace station is located directly in front of an air conditioning fan's air path, application 1102 may make reservation decisions based on this. These may include marking the entire room in which the workplace station is located as hazardous, as there is a possibility that the contagions from the hazardous workplace station were spread via the air pathways of the air conditioning fan.

These decisions may also include marking other desks in the airflow path as hazardous. Airway path direction, the effects of the airway paths, and the risk associated with a user working within an airway path may be considered by the application (e.g., a processing circuit processing the input data for application 1102, etc.). For example, workplace station that is located within an air pathway has an effect on reservations of other workplace stations within the air pathway. Once the first workplace station is unreservable, all other workplace stations may be unreservable as a result. Sensors located within the workspace that includes multiple workplace stations may provide air data (e.g., air velocity, direction of air flowing past the sensor, etc.) to infection transmission risk manager 101 to determine a particular air pathway within the workspace. Manager 101 may also include a mapping of the workplace stations within the workspace. In one embodiment, manager 101 maps the air pathway determined by the air data to the workplace stations to determine which workplace stations are located within the determined air pathway(s). In some embodiments, a monitored area (e.g., the workspace, a location being monitored for contagious diseases, a workplace station, etc.) may be considered higher-risk, as a workers respiratory droplets may be carried on the airflow. Conversely, the risk may be considered lower when there is little or no occupancy in the workplace.

The viability of a workplace station may also be considered when using application 1102. For example, if a particular workplace station is at a position that will greatly affect other workplace stations, that particular workplace station may be unreservable simply due to its location. In some embodiments, the workplace stations within higher-risk areas (e.g., within an airflow path, near an area of heavy foot traffic in the workspace, etc.) are unreservable as well due to their location.

In some embodiments, infection transmission risk manager 101 or another processing component responsible for managing the reservations may include a machine learning (ML) model that trains to develop the effects that airway paths have on transmitting contagious diseases. For example, the ML model is a supervised model wherein a manager of the ML model (e.g., a technician, a building engineer, etc.) supervises the spread of an infectious disease when the disease enters the air pathway(s). The ML model may include algorithms that input air pathway data (e.g., the air data as described above, etc.) and locations of the workplace stations in the workspace and outputs a level of contagious risk for the workplace stations within the air pathway(s). While the above example utilizes a supervised ML model, unsupervised ML models may also be considered. Furthermore, several types of machine learning algorithms may be implemented, such as linear regression models logistic regression models decision trees Naive Bayes algorithms, k-nearest neighbor (KNN) algorithms, and random forest algorithms.

Infection transmission risk manager 101 may use the output of the ML algorithm to send notifications to users of application 1102 that have workplace stations within the air pathway(s) indicating the predetermined level of contagious risk of their workplace station determined by the ML algorithms. In some embodiments, the outputs from the ML model are integrated with the HVAC system supplying air conditioning to the workspace to mitigate the spread of the infectious disease throughout the air pathway. For example, if there are multiple HVAC vents located within a workspace, the flow rates of the boiler/chiller fluid for air conditioning for air exiting the multiple HVAC vents could be adjusted to maintain the required overall flow rate, but reductions in some areas to reduce the chance of transmission. The ML model and/or manager 101 may also be integrated with a sanitization system (e.g., hygiene system 105 as described above) such that sanitization can be automatically implemented in areas that do not conform to some or all of the social distancing rules (e.g., locations that are indicated so in a heat map, etc.).

In some embodiments, the ML model is trained prior to being implemented with infection transmission risk manager 101. For example, the machine learning model uses 3-4 months of workspace station reservations as training data to determine how impactful the presence of contagious workplace stations are in the air pathways and proximate to the air pathways.

In some embodiments, application 1102 may also include machine learning functionality that allows application 1102 to learn traffic patterns, air flow pathways (as discussed above), and/or high-risk zones of the floor to better determine the hazardous locations within the floor, particularly with regards to which workplace stations are hazardous. Application 1102 may retrieve information from manager 101 that indicates the contagious risk of the workplace stations within the workspace. Manager 101 may also provide a heat map of the contagious areas within the workspace. In some embodiments, the heat map is determined by the ML model by determining a model from the outputs of the air pathway calculations in the example described above.

In some embodiments, application 1102 may be configured to provide recommendations for arranging workspaces to meet certain goals or rules, such as social distancing rules. For example, application 1102 may provide functionality to reconfigure a workplace within building 10 to reduce desk density and meeting room capacity in order to meet social distancing guidelines. Manager 101 may receive data on the number of reservations within the workspace for a particular day and the total number for workplace stations within the workspace. Manger 101 may also receive data on any contagious risk indications from previously-reserved workplace stations and/or air pathway(s) effects. In some embodiments, manger 101 compares the received reservation and contagious risk data and compares it to social distancing rules to determine which, if any, workplace stations need to be unreservable or removed to satisfy the social distancing rules. This might include sending a notification to a building workers (e.g., maintenance works) or integrating the maintenance scheduling system with manager 101 to facilitate a reduced workstation capacity in the workplace.

In some embodiments, manager 101 provides cleaning (e.g., sanitization, etc.) instructions to hygiene system of another systems configured to sanitize the workplace. This may be done in response to determining which workplace stations are not reservable and/or which desks are not conforming to social distancing rules. For example, upon manager 101 determining the outputs of the ML model indicating which workplace stations in a particular air pathway may have been affected, manager 101 may provide control signals to hygiene system 105 instructing hygiene system 105 to adequately sanitize the workplace station such that it may conform to social distancing rules. This may include automatically casting ultra violet light (e.g., UVA light, UVB light, UVC light, etc.) via UV lights located proximate to the workplace station. In another embodiment, this includes integrating hygiene system 105 with a maintenance schedule such that a maintenance worker or custodian can be instructed to go to the workplace station and manually sanitize the workplace station.

In some embodiments, application 1102 may be configured to lower office occupancy. For example, application 1102 may reduce the number of people working in the office to a safe level following a significant reduction in available desks due to social distancing. In some embodiments, application 1102 facilitates improved sanitization of workplaces within building 10. For example, application 1102 may ensure that workspace cleaning is enforced when desks are scheduled to be used by a different employee or for an employee that plans to use a nearby desk in the near future. To reduce the workplace of cleaning and sanitizing workplace stations for future reservations, the workplace stations that are not switching users may not need to be sanitized, as the user is incapable of spreading the disease to themselves.

In some embodiments, application 1102 includes contact tracing to monitor peer-to-peer contact. For example, application 1102 may record the workplace stations reserved and the users that have reserved the workplace stations to determine who has been exposed to a contagious disease in the event that one of the users who reserved a workplace station has tested positive for the contagious disease. Manager 101 may receive this data from application 1102 and data regarding contact throughout the workday (e.g., when a co-worker enters a certain office, etc.). In the event that manager 101 receives an indication that at least one of a worker in the workplace or a workstation may have come into contact with an infectious disease, manager 101 can analyze the received data and provide notifications to individuals who may have come into contact with the infected area or person. Manager 101 may also begin a sanitization process by providing control signals to hygiene system 105 instructing hygiene system 105 to sanitize workplace stations that the infected person may have come into contact with. Manager 101 may also update the reservation system (e.g., application 1102). Workplace stations used by potential contacts could be unreservable until cleaned. They may be reservable if subsequently cleaned, or for additional safety, all become unreservable until a deep clean is performed.

In some embodiments, manager 101 defines or implements a minimum distance of separation that occupants must maintain to reduce the possibility of transmitting an infectious contagion. Manager 101 may implement this rule by tracking the positions of occupants within the workspace. This may be done using trackers, video monitoring, or other methods. The monitoring data may then be sent to manager 101 in the event that contact tracing needs to be implemented. In some embodiments, manager 101 monitors the data and determines that a distance between two occupants is closer than the minimum distance of separation that occupants must maintain to reduce the possibility of transmitting an infectious contagion. Manager 101 may then notify building occupants via application 1102 and/or implement steps to resolve the issue.

In some embodiments, manager 101 implemented these dynamic workspace reservation systems based at least in part on safety rules and/or social distancing guidelines. In some embodiments, the safety rule includes a safety threshold that is based on a period of time since a hazardous incident has occurred at the workplace station, a risk level associated with the contagious disease, an amount of sanitization that was performed at the one of the plurality of workplace station, or any combination thereof. The safety rule may also include a requirement that adjacent workstations or workstations within a threshold distance of one another must be unoccupied for the threshold amount of time for the workstations to be reservable. In some embodiments, the safety rule is based on occupancy of adjacent workstations or workstations within a threshold distance of one another. The threshold distance may define a circular region centered around a hazardous workplace station, or a conical or ovoid shape depending on the direction that a person is facing. In other embodiments, it could be affected by the surrounding environment (e.g., people may occasionally stare out through a window while working, etc.) so that could affect the shape of the risk area. In some embodiments, eye-tracking at the workstation is used to determine the shape of the threshold perimeter.

In some embodiments, application 1102 includes functionality to keep building occupants (e.g., workers, managers, etc.) informed of hazardous situations. For example, application 1102 provides constant or periodic updates to building occupants (e.g., via text messages, emails, via application 1102, etc.) to notify them of changes to available workplaces, zones, and/or locations in building 10, updates on contact tracing, and other information related to reservations and/or contagious diseases within building 10.

Figure 12:
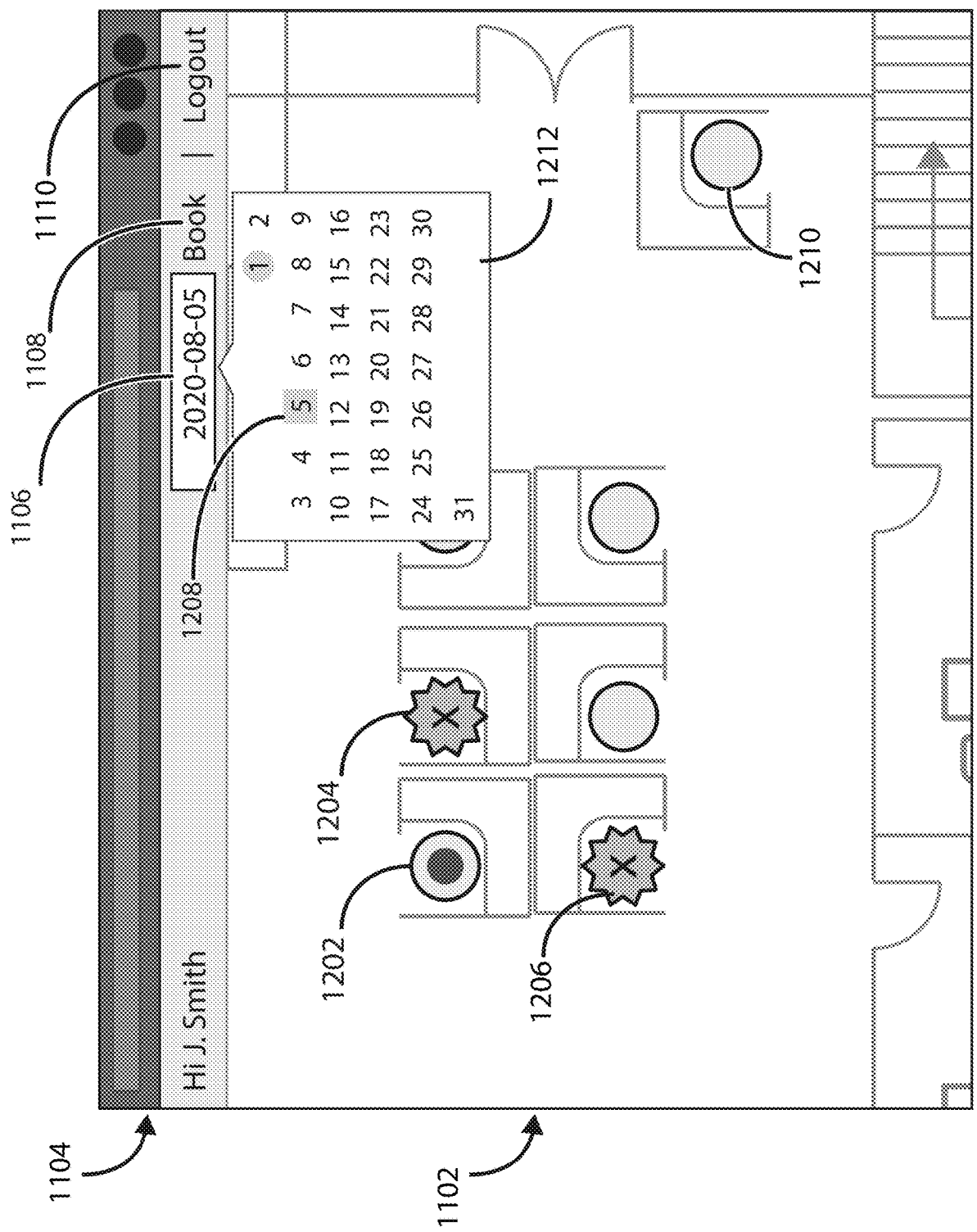
FIG. 12 is a diagram of a user interface for reserving workplace stations, according to some embodiments.

Referring now to FIG. 12 application 1102 includes workplace stations 1202-1206 and selected date 1208. In some embodiments, the user may select another date (e.g., a date different than the date selected in FIG. 11), which may show different reservation options. As shown in FIG. 12, the user wishes to reserve workplace station 1202. However, workplace stations 1204-1206 may be hazardous workstations. A hazardous workstation may refer to workstations that have recently been used. For example, a worker may have worked in that workstation recently (e.g., within 24 hours, etc.). As such, the workstation may present a hazardous problem to nearby workstations due to the spread of contagious pathogens that may spread. In some embodiments, a hazardous workstation refers to a workstation that has not been properly sanitized. This can include cleaning the workstation with anti-bacterial and/or other cleaning products to mitigate the contagious pathogens at the workstation. Once the workstation has been sanitized, application 1102 may allow a user to reserve that workstation again. The sanitization times may be scheduled automatically, scheduled based on the reservations, scheduled based on the density of nearby workplace stations, or any combination thereof. For example, a sanitization order is provided to a custodian and is not completed by the next day. A reservation for that morning will be denied and a message is provided to the user attempting to reserve the workplace station, indicating that the workplace station has not been properly sanitized.

In other embodiments, a user may reserve workplace station 1202, but cannot reserve workplace stations 1204, 1206 as they are recently hazardous, but are not currently being used. Another user may have used workplace station 1204 recently (e.g., 1 day ago, 2 days ago, etc.) and as such, workplace station 1204 is still considered contaminated. In various embodiments, workplace stations may be considered hazardous (such that they cannot be reserved) based on location (e.g., near another hazardous workplace station, near a contaminated region in the building, etc.), time (e.g., only 4 hours since a user used the workplace station, etc.), sanitization (e.g., a custodian has not sanitized the workplace station recently, etc.), and any combination thereof.

In some embodiments, the location of the workplace station makes a considerable impact on reservations of other workplace stations within the room. For example, if workplace station 1204 was located right next to the doorway of the room, and workplace station 1204 was considered hazardous, then every other workplace station may be considered unreservable (e.g., hazardous), as an individual would have to walk by workplace station 1204 and possibly transfer the contamination to another workplace station or stations. Additionally, various symbols may be used to indicate reservation stations, limitations, hazardous workplace stations, and other features. For example, workplace station 1112 shows a person emblem within the selectable circle. This may indicate that the current user has functionality to reserve only that particular workstation. FIG. 12 shows workplace station 1202 with a circle within the selectable circle. This may indicate that the current user does not have functionality to reserve workplace station 1202, as nearby workplace stations (e.g., workplace stations 1204, 1206) are considered hazardous. Application 1102 may generate reports related to this and provide the reports to a third party, human resources (HR), or another database for further analytics.

Figure 13:
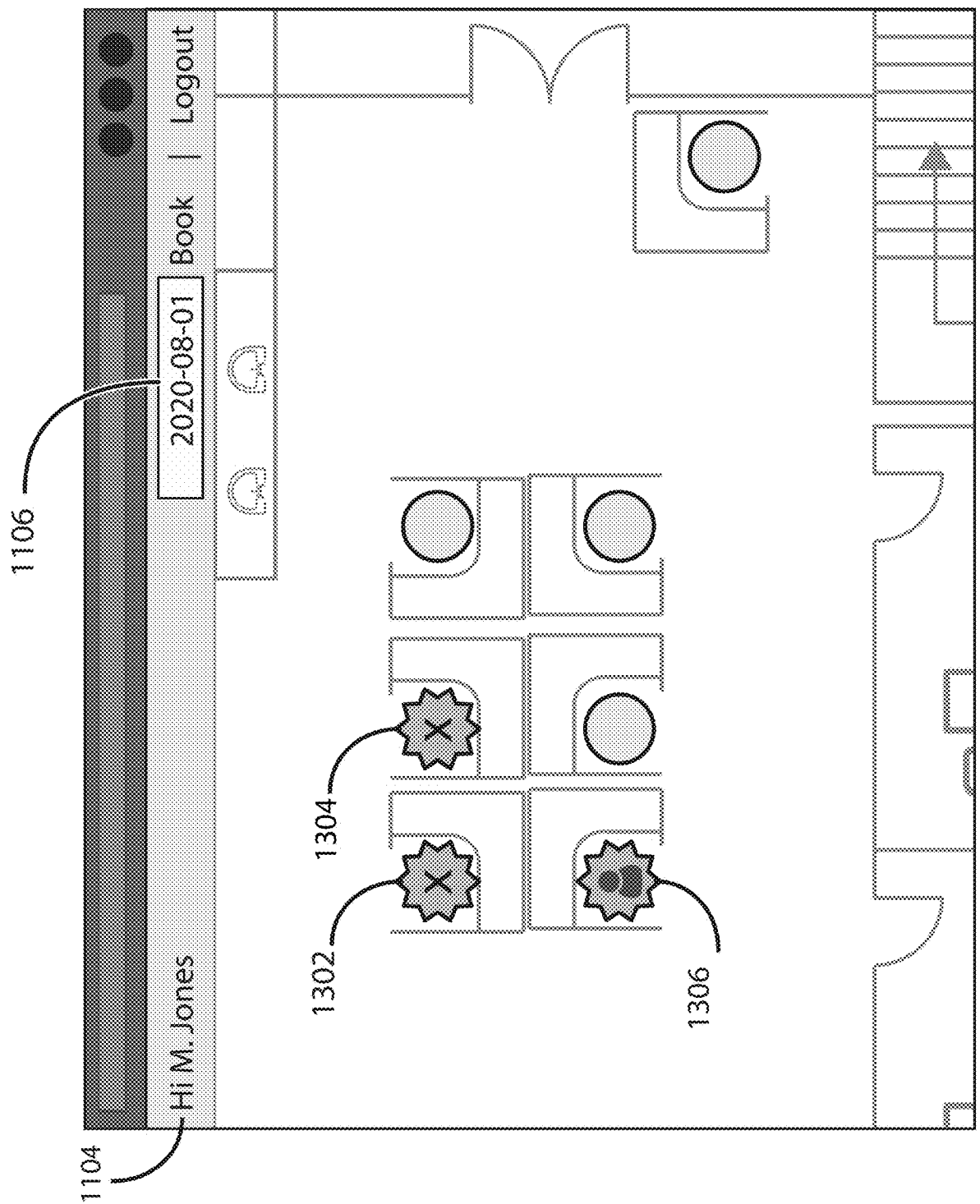
FIG. 13 is a diagram of a user interface for reserving workplace stations, according to some embodiments.

Referring now to FIG. 13, another view of application 1102 is shown, according to some embodiments. FIG. 13 shows the reservations of the various workplace stations from the perspective of another user—the user who can reserve workplace station 1306. In some embodiments, FIG. 13 shows the same reservations as shown in FIG. 12, but from another user interface. The user for application 1102 as shown in FIG. 13 may be attempting to reserve workplace station 1306, but is unable to due to workplace stations 1302, 1304 being considered hazardous. In some embodiments, workplace station 1302 is workplace station 1202 after it had been reserved by another user. Now, in FIG. 13, workplace station 1306 cannot be reserved as it is next to workplace station 1302 which has already been reserved.

Figure 14:
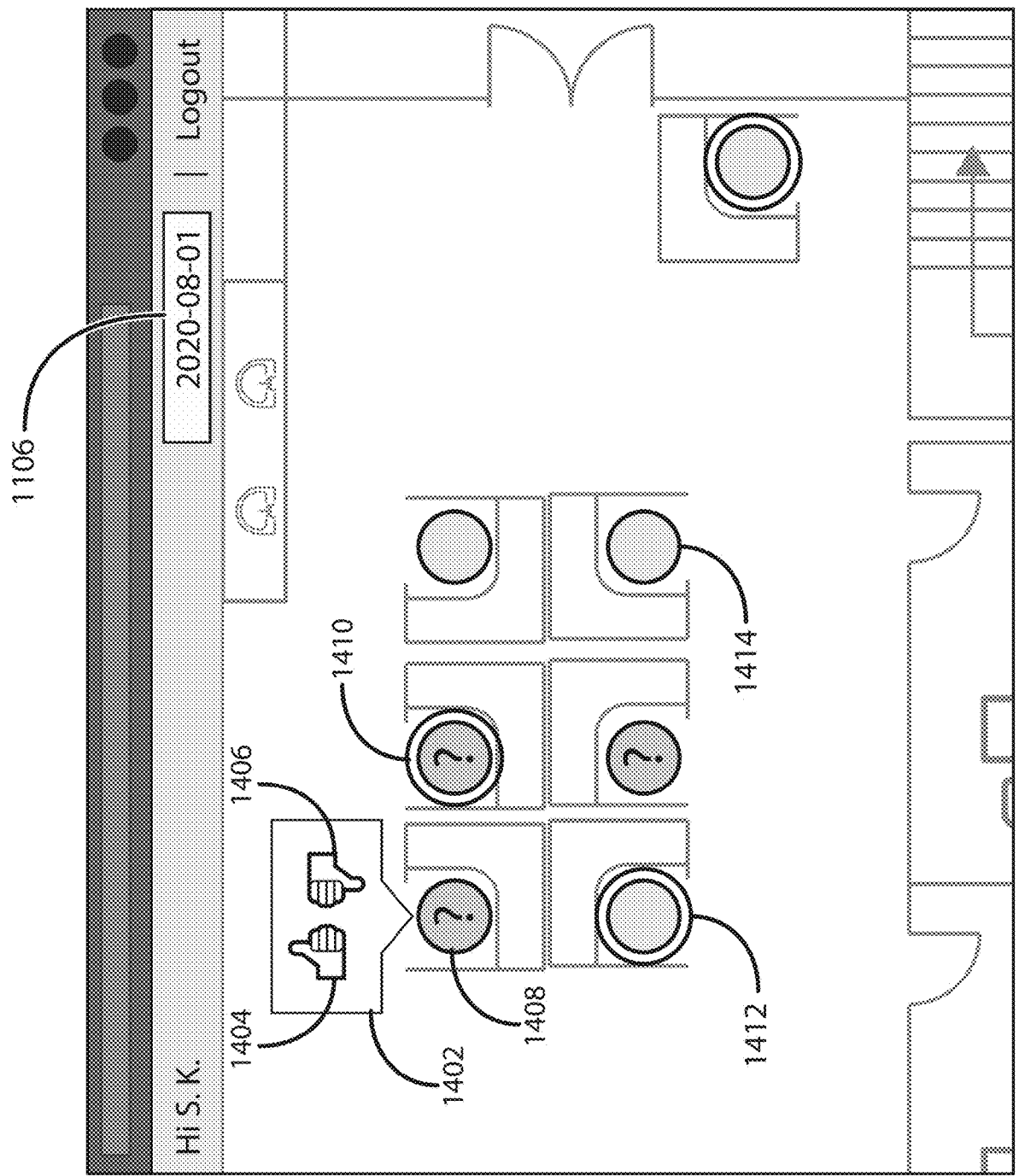
FIG. 14 is a diagram of a user interface for managing workplace station reservations, according to some embodiments.

Referring now to FIG. 14, a user interface showing application 1102 from a managerial perspective is shown, according to some embodiments. FIG. 14 is shown to include selection window 1402, approve widget 1404, decline widget 1406, and workplace stations 1408-1414. In some embodiments, a manger may confirm reservations and resolve various reservation conflicts occurring within application 1102. For example, a manger selects a date from date button 1106 to bring up a visual of the various workplace reservations. Workplace stations that have a reservation on that date are indicated so by a question mark symbol (e.g., the question mark system on workplace stations 1408-1414). A manager may engage selection window 1402 and approve or decline the requested reservation for workplace stations 1408-1414 via approve widget 1404 and decline widget 1406, respectively. In some embodiments, the user may receive a notification (e.g., email, text, notification via application 1102, etc.) regarding the decision of their requested reservation. Those workplace stations that do not have a requested reservation are indicated so by a plain marker, as shown in FIG. 14.

Figure 15:
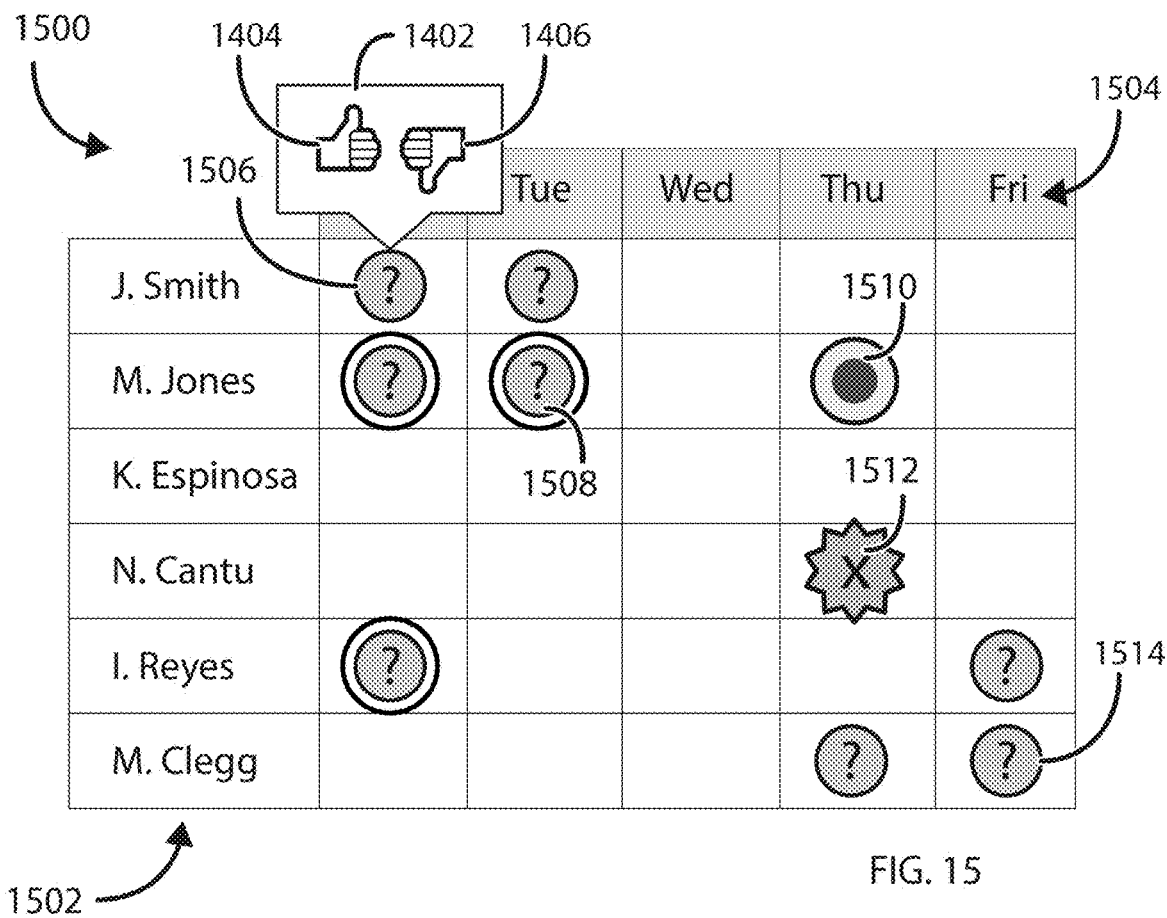
FIG. 15 is a diagram of a chart for managing workplace station reservations, according to some embodiments.

Referring now to FIG. 15, another interface for resolving requested reservations is shown, according to exemplary embodiments. FIG. 15 is shown to include table 500 including row headings 1502 and column headings 1504. Table 500 further includes reservations 1508-1514. Application 1102 may implement table 500, including selection window 1402 as described above with reference to FIG. 14. In some embodiments, a manager opens table 500 to determine various reservation requests. As shown in FIG. 15, reservation request 1508 may indicate that M. Jones requested a reservation for his/her workplace station on Tuesday. The manager can then approve or decline the reservation via selection window 1402. Confirmed reservations may change in their visual appearance, such as reservation 1510, which may indicate that the reservation request from M. Jones for Thursday has been approved. Blocked reservations also change in their visual appearance, such as reservation 1512, which may indicate that the reservation request from N. Cantu on Thursday is declined. In various embodiments, the systems and methods for approving or declining reservation requests may be identical or substantially similar to those described above with reference to FIG. 14, but are merely represented in a different fashion in application 1102, such as in table 500.

In some embodiments of FIG. 15, the icons for the workplace stations that would be blocked by the approval of the reservation indicated by icon 1506 are highlighted—shown with circle outlines in FIG. 15. Additionally, the risk of workplace stations may be stacked, such that an increase in risk to a nearby workplace station does not necessarily make the workplace station unreservable. Manager 101 may include logic that implements a risk threshold such that, when a workplace station's risk level reaches the threshold, the workplace station is considered unreservable. The risk level may increase based on different risk actions occurring within the workplace, such as a nearby contagious workplace station, contact tracing, airflow path exposure, and other actions.

Figure 16:
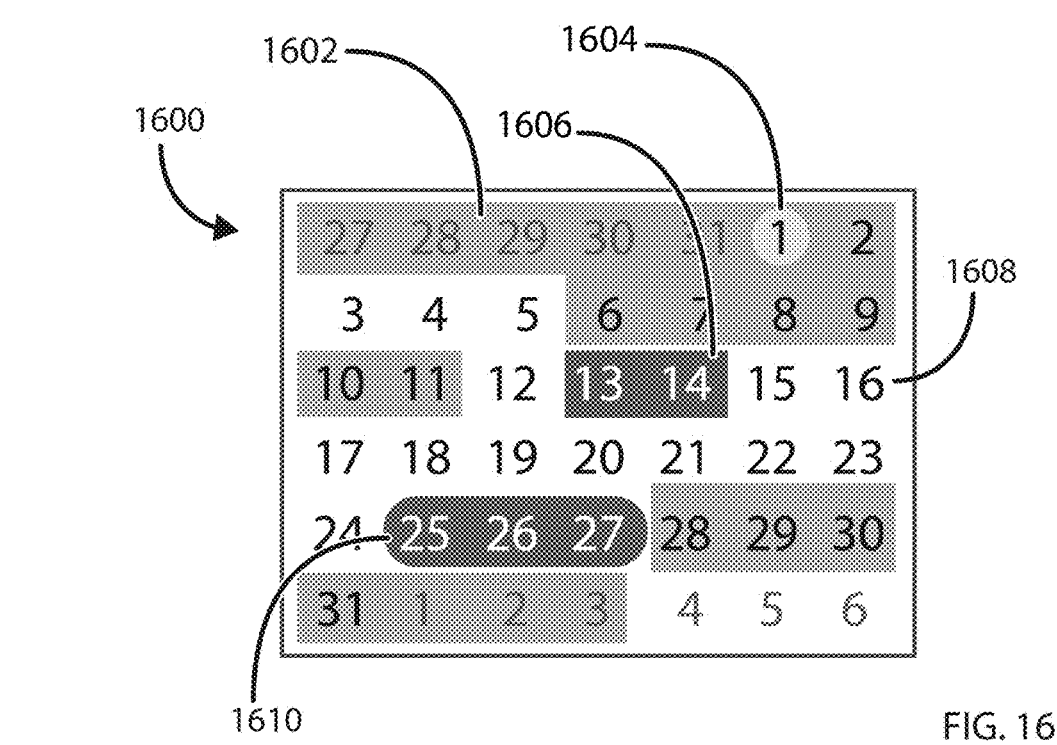
FIG. 16 is a diagram of a calendar for viewing workplace station reservations, according to some embodiments.

Referring now to FIG. 16, a calendar for displaying reservation information is shown, according to exemplary embodiments. FIG. 16 is shown to include calendar 1600, including blocked reservation dates 1602, current date 1604, previously booked dates 1606, available reservation dates 1608, and user interface (UI) element 1610. Calendar 1600 may be a feature of application 1102 that allows one or more users (e.g., managers, users requesting reservations, etc.) to view the reservation information for one or more months, rather than on a daily basis. Calendar 1600 may allow the user's to see which dates are still available for reserving, and which dates are unavailable. Calendar 1600 may also indicate which reservation requests have been approved and declined.

Dynamic Co-Working Spaces

Figure 17:
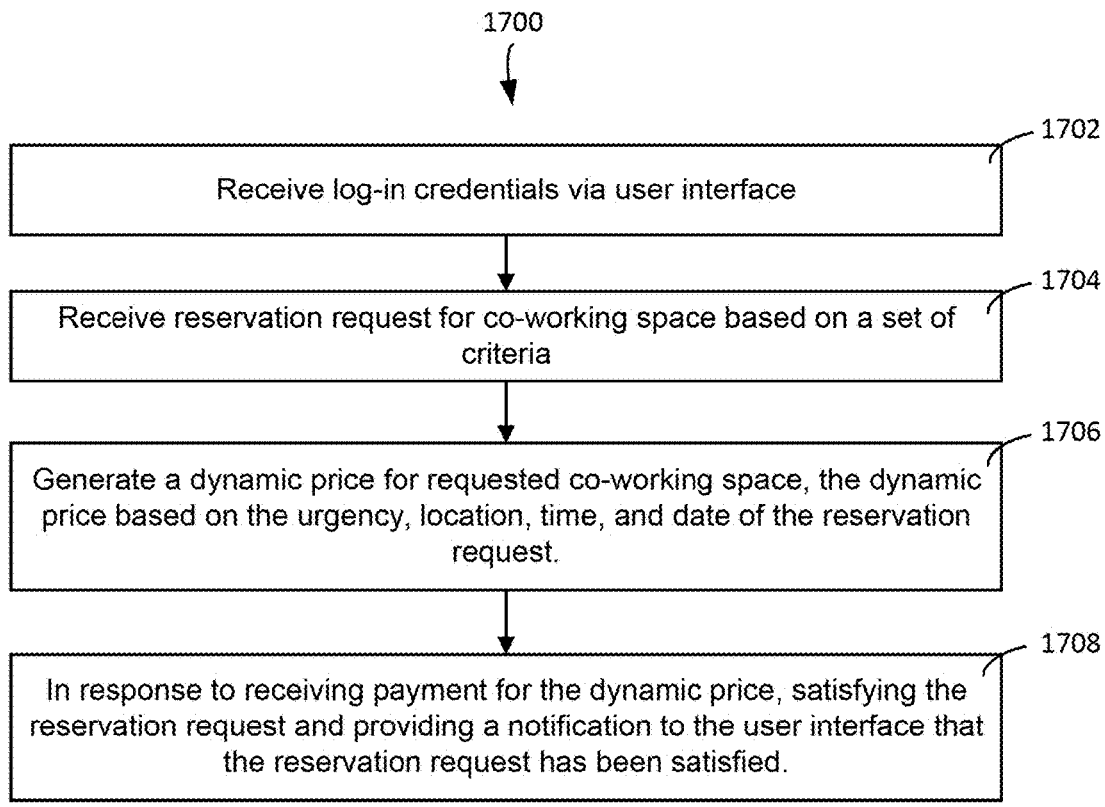
FIG. 17 is a flow diagram of a process for performing reservation transactions which can be implemented by the application of FIG. 11, according to some embodiments.

Referring now to FIG. 17, a flow diagram of process 1700 for providing co-working reservations to users is shown, according to some embodiments. In some embodiments, the systems and methods disclosed herein regarding reservations of workspaces may be expanded to buildings, industries, and businesses outside of building 10. For example, building 10 and another business (e.g., a business that operates in a different industry than building 10, etc.) may be "co-working" entities. In some embodiments, this refers to a relationship between the buildings that allows employees of building 10 to make reservation requests for workspaces at building 10 and/or the other building.

Process 1700 is shown to include receiving log-in credentials via a user interface (process 1702). As described above, user device 107 can host an application (e.g., application 1102, etc.) configured to allow a user to reserve, monitor, and adjust reservations for workspaces in a building. In some embodiments, it is more convenient and/or accessible to an employee/worker of building 10 attempting to reserve a workspace. A user may supply log-in information via application 1102 on user device 107, such as name, address, username, password, etc.

Process 1700 is shown to include receiving reservation requests for co-working space based on a set of criteria (step 1704). In some embodiments, an employee of building 10 may request a workspace over the application for a workspace located in a building other than that of building 10. In some embodiments, building 10 may be at capacity for reservations by the time the user attempts to reserve a workspace in building 10. In other embodiments, there may be a price for reserving a workspace and the pricing for workspaces at the other building are lower than those of building 10. Dynamic pricing of workspaces is discussed in greater detail below.

Process 1706 is shown to include generating a dynamic price for a requested co-working space, the dynamic price based on the urgency, location, time, and date of the reservation request (process 1706). Of course, more or less of these criteria can be considered for adjusting the price for the workspace. In some embodiments, the price of a workspace can be similar to the price of a ride-sharing vehicle (e.g., Uber, etc.). During busier times (e.g., times in which more reservations will be requested such as 9:00 AM on a Monday, etc.), the pricing can increase. In contrast, reserving a time that there is relatively low traffic in the other building (e.g., 2:00 AM on a Saturday), the price can decrease significantly. As workspaces fill up, the pricing can also increase for the workspaces.

In some embodiments, the sale of the workspace (e.g., a location, cubical, table, or desk within the other building) is facilitated by the owner/administrators of the other building. The owner of the other building and the owner or building 10 may reach an agreement where the employees of building 10 are allowed to reserve workspaces not only in building 10, but now also in the other building, where the owner of the other building can collect profits from renting out their space within their building as workspaces for employees. Of course, other individuals/teams can facilitate the transaction agreements between the employees of one building and the reservation spots of another building apart from owners, such as managers, vice presidents, etc. In some embodiments, the profit margin from the reservation transactions can be received by the owners of the other building, the owners of building 10, a third party (e.g., an application developer of application 1102, etc.) or a combination thereof.

In some embodiments, several criteria can affect the dynamic pricing of the workspace. For example, the price of a workspace may be more expensive to reserve if the user is attempting to reserve the workspace in a very short time frame (e.g., requests a 2-hour reservation starting in 10 minutes, etc.) compared to if the user reserves a workspace for a period father in the future (e.g., several days or weeks out, etc.). In some embodiments, the duration of the reservation can also affect the price of the workspace. For example, a five minute reservation may be significantly cheaper than a reservation for a 3 hours (e.g., with all other criteria constant, etc.).

Process 1700 is shown to include, in response to receiving payment for the dynamic price, satisfying the reservation request and providing a notification to the user interface that the reservation request has been satisfied (process 1708). In some embodiments, application 1102 can present what the workspace would cost at that time and place, and the user can select whether they finalize the reservation request after they have been notified of the price. In some embodiments, the price is dynamically generated for each new reservation request, as the location of the workspace, the time of the reservation request, the capacity of the building, and the urgency of the request (e.g., request for a workspace in 5 minutes, etc.) can all play a role in adjusting the price of the workspace. The pricing dynamics are described in greater detail below with reference to FIG. 19.

Figure 18:
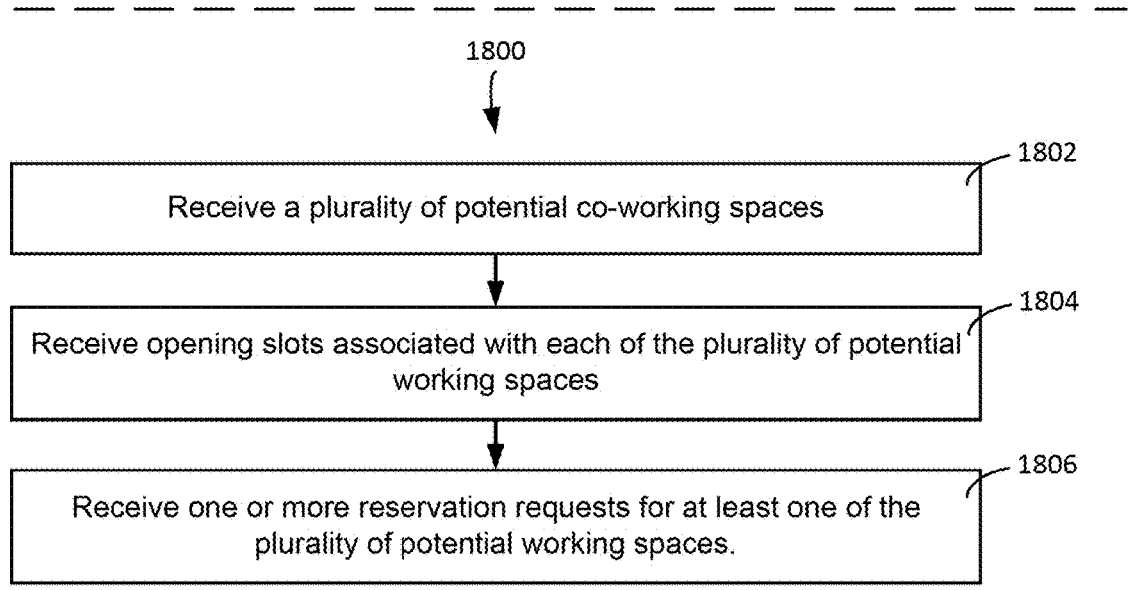
FIG. 18 is a flow diagram of a process for facilitating reservation requests with multiple co-working spaces which can be implemented by the application of FIG. 11, according to some embodiments.

Referring now to FIG. 18, a process 1800 for dynamically scheduling time slots of workspaces, according to some embodiments. Process 1800 (and similarly process 1700 as described above) can be performed by any of the processing components described herein, and may be performed by a server or other processing circuit that stores, hosts, and/or processes application 1102. In some embodiments, buildings may only be able to provide workspaces for rent/reservation requests at certain points of the day and/or for select locations within the building (e.g., only for certain tables, certain areas, etc.).

Process 1800 is shown to include receiving a plurality of potential co-working spaces (step 1802) and receiving opening slots associated with each of the plurality of potential working spaces (step 1804). In some embodiments. In some embodiments, application 1102 can receive multiple spaces that are available for reservation that can be displayed on user device 104. In some embodiments, one or more of the workspaces are available only for certain times. For example, the tables at a restaurant of a building are only available during closed hours or the restaurant or during slow hours in the restaurant, so as to not interfere with the regular day-to-day business of the restaurant.

In some embodiments, the time of availability of the workspaces, the particular workspaces available, the location of the available workspaces, or a combination thereof is changing constantly (e.g., in real-time, updated every 5 minutes, updated every 10 minutes, etc.). This can be based on new reservations being secured (e.g., requested and/or satisfied, etc.), changes in the business (e.g., adding new workspaces, removing workspaces, etc.), and/or policy updates (e.g., COVID-19 restriction updates, social distancing updates, etc.).

Process 1800 is shown to include receiving one or more reservation requests for at least one of the plurality of potential working spaces (step 1806). The user can then select one (or more) of the workspaces to reserve. To note, while the systems and methods disclosed herein are generally relating to workplace buildings (e.g., corporate offices, laboratories, administrative floors, office spaces, etc.) various other locations may be considered, such as hospitals, pharmaceutical labs, and storage facilities. For example, a patient who was recently treated in hospital bed that tested positive for a contagious disease may result in the hospital bed being a hazardous station for a period of time.

Additionally, the "other buildings" referred to herein can refer to any type of location separate from building 10 capable of leasing, providing, renting, or hosting workspaces for individuals or teams that can be reserved, as described above. These can include other buildings, floors of other buildings, outside seating (e.g., of a restaurant), an office building, a large residence, and warehouses.

Intelligent Pricing

Figure 19:
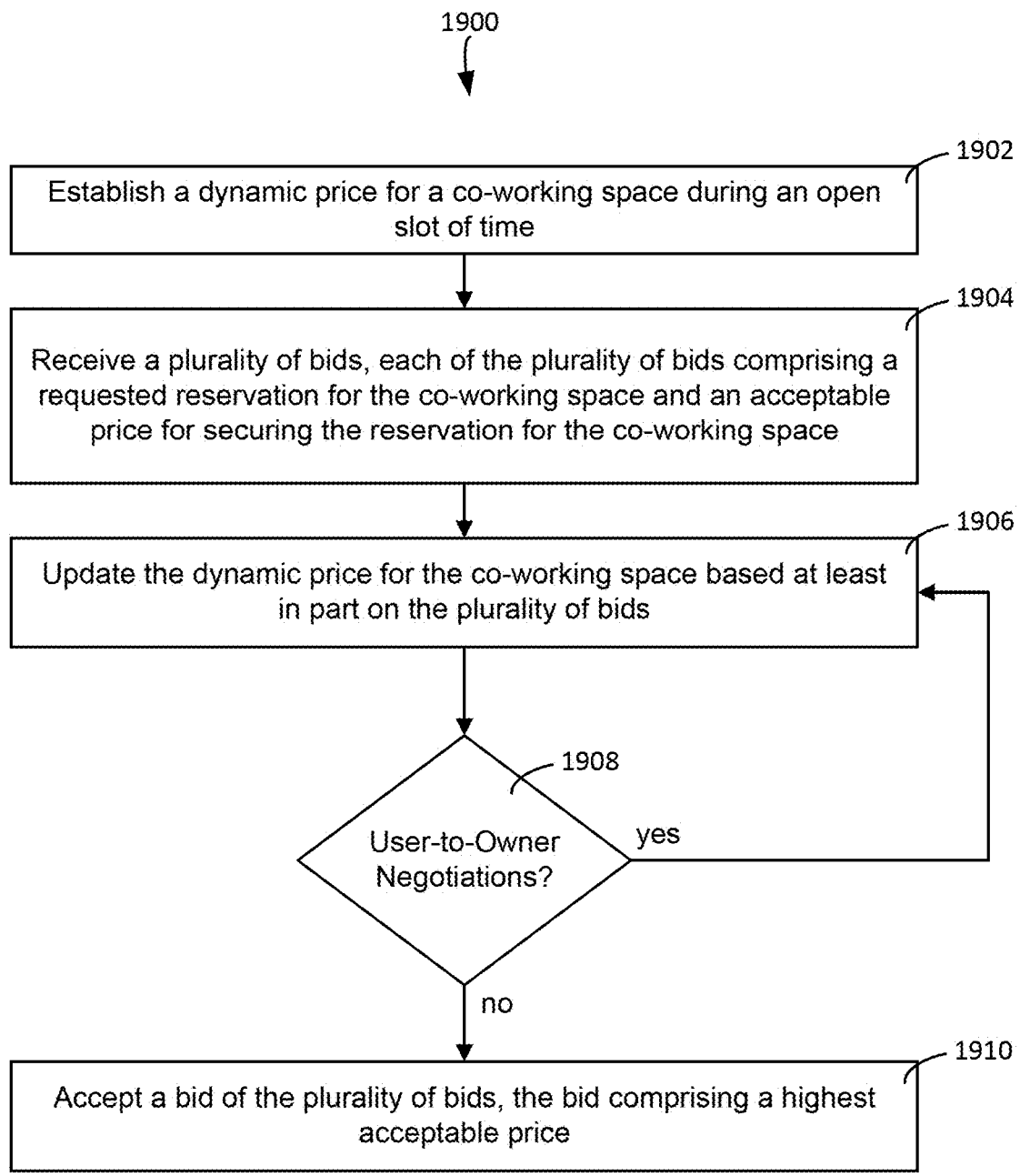
FIG. 19 is a flow diagram of a process for performing reservation transactions which can be implemented by the application of FIG. 11, according to some embodiments.

Referring now to FIG. 19, a process 1900 for adjusting the dynamic price for a workspace reservation based on multiple received bids, according to some embodiments. Process 1900 can be performed by any of the processing components described herein, and may be performed by a server or other processing circuit that stores, hosts, and/or processes application 1102. In some embodiments, process 1900 is implemented by application 1102 to increase profit margins of the owner (e.g., distributor of application 1102, the owner of the building that is providing the workspace, the owner of the business in for which the user is employed by, a combination thereof, etc.).

Process 1900 is shown to include establishing a dynamic price for a co-working space during an open slot of time (process 1902). In some embodiments, an initial price point is set for a workspace. This can be a standard price for a workspace not influenced by the dynamic pricing adjustments discussed below. In other embodiments, the price point is always based on the dynamic pricing adjustments.

Process 1900 is shown to include receiving a plurality of bids, each of the plurality of bids comprising a requested reservation for the co-working space and an acceptable price for securing the reservation for the co-working space (step 1904). In some embodiments, multiple users are providing requests for a single workspace. This results in an increase in the price of the workspace, as demand has increased. Of course, the price can also change in part based on the other criteria mentioned above (e.g., location, time of day, etc.).

Process 1900 is shown to include updating the dynamic price for the co-working space based at least in part on the plurality of bids (process 1906). This can be performed a number of ways using any number of algorithms. In one non-limiting example, an equation (e.g., objective function, etc.) is implemented with varying weights for a base rate, surcharges (e.g., based on prime location, etc.), surge pricing, discounts (e.g., premium member benefits, etc.), and/or group rates. In some embodiments, a number of discounts can included in determining the dynamic price of the workspace. These can include benefits from a membership purchased for application 1102, promotional discounts, sales, or other techniques to decrease the price of one or more workspaces. In some embodiments, a number of surcharges can be applied (e.g., in addition to discounts, etc.).

In another non-limiting example, a the dynamic price starts at a base and increases/decreases incrementally based on changes to the overall system. For example, the base price begins at $10.00 for reserving a workspace. Based on the time requested for the reservation being 9:00 AM on a Monday, the price increases to $14.00. The user inputs a promotional code due to their rewards on their membership account from using the application, which decreases the price to $9:00. The reservation request is for two full days, which increases the price to $15.00. The user then submits the request and provides payment for the reservation. In the above example, any number of price adjustments can be implemented at any point and/or in any order.

Process 1900 is shown to include determining if user-to-owner negotiations (step 1908). In some embodiments, a negotiation may occur between the owner (e.g., distributor of application 1102, the owner of the building that is providing the workspace, the owner of the business in for which the user is employed by, a combination thereof, etc.) and the user. In other embodiments, a negotiation may occur between the owner and another party within the system (e.g., application developer, owner of building 10, etc.). These can include negotiations between profit margins, negotiations between the algorithms for determining the dynamic pricing, or negotiations between a direct sale (e.g., the user discusses a price change directly with the owner, etc.).

For example, the owner of building 10 (e.g., where the employees of building 10 are the users of application 1102, etc.) negotiates with the owner of the other building on a profit split adjustment. This adjustment may have an effect on the dynamic pricing, which can be updated upon completion of the negotiations (back to step 1906). In the event that no further user-to-owner negotiations are considered, process 1900 proceeds to step 1910.

Process 1910 is shown to include accepting a bid of the plurality of bids, the bid comprising a highest acceptable price (step 1910). In some embodiments, a key factor of the dynamic pricing is the increase in price based on the number of bids. As the quantity of bids increases, the price provided to users for subsequent bids increases. Thus, the final bid is the bid with the highest reservation price that a user is willing to pay. Of course, the price may further be affected by any of the criteria and/or methods described above. In some embodiments, the term "data" may be or include, at least partially or entirely, user interface data.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and are considered to be within the scope of the disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

What is claimed is:

1. A method for mitigating risk of transmission of a contagious disease in a building, the method comprising:
    determining, by a processing circuit comprising one or more processors, a safety rule to be applied to a workspace comprising a plurality of workspace stations, the safety rule relating to limiting the transmission of the contagious disease, wherein the safety rule is based on occupancy of adjacent workstations or workstations within a threshold distance of one another, and the safety rule includes prohibiting reservation of a workspace station based on an adjacent/proximal workspace station being occupied at the time for which the reservation is requested;
    receiving, at the processing circuit, a request for one or more reservable workspace stations, the request comprising one or more request parameters;
    identifying the one or more reservable workspace stations from among the plurality of workspace stations by determining, by the processing circuit, whether to permit the one or more reservable workspace stations to be reserved based on the safety rule; and
    generating, by the processing circuit, data identifying the one or more reservable workspace stations.

2. The method of claim 1, wherein determining the safety rule to be applied to the workspace comprises determining a safety threshold based on at least one of:
    a period of time since a hazardous incident has occurred at the workplace station,
    a risk level associated with the contagious disease, and
    an amount of sanitization that was performed at the one of the plurality of workplace station.

3. The method of claim 1, wherein:
    the one or more request parameters comprises a timing parameter,
    the safety rule comprises a threshold amount of time the workspace stations must be unoccupied after a last occupant; and
    identifying the reservable workspace stations comprises determining that the workspace station has been unoccupied for at least the threshold amount of time.

4. The method of claim 3, wherein the safety rule further comprises a requirement that adjacent workstations or workstations within a threshold distance of one another must be unoccupied for the threshold amount of time for the workstations to be reservable.

5. The method of claim 1, wherein determining whether to permit the workspace stations to be reserved based on the safety rule comprises:
    determining that the one or more workspace stations are not reservable based on the safety rule; and
    implementing an automated sanitizing feature or a notification to a building occupant to sanitize the one or more workspace stations such that the one or more workspace stations are reservable, wherein the automated sanitizing feature comprises at least one of sanitizing light or ultraviolet violet A (UVA) light, UVB light, or UVC light.

6. The method of claim 5, wherein the method further comprises generating graphical user interface (GUI) data that provides visual indicators to a GUI to indicate whether the workspace stations are reservable or not reservable.

7. The method of claim 6, wherein determining whether to permit the workspace stations to be reserved based on the safety rule comprises:
determining at least one of an indication of the reason for the restriction and a time in which the restriction will be lifted; and
providing the at least of the indication and the time to the GUI.

8. The method of claim 7, wherein determining at least one of the indication and the time in which the restriction will be lifted comprises determining whether the time in which the restriction will be lifted has occurred or will occur, wherein:
in response to determining the time has occurred, provide a first notification to the GUI; and
in response to determining the time will occur, provide a second notification to the GUI.

9. The method of claim 1, further comprising:
generating, by the processing circuit, a price for reserving the one or more reservable workspace stations;
providing the price and the one or more reservable workspace stations to a user interface;
receiving, via the user interface, an input indicating a payment satisfying the price; and
in response to receiving the payment, satisfying the request to reserve the one or more reservable workplace stations.

10. The method of claim 9, wherein generating the price for reserving the one or more reservable workspace stations comprises:
receiving a plurality of bids for the one or more reservable workspace stations, wherein each of the plurality of bids is provided using a corresponding user interface; and
updating the price based on the number of received bids of the plurality of bids.

11. The method of claim 1, wherein receiving the request for one or more reservable workspace stations comprises receiving the request for one or more reservable workplace stations located in a location separate from the building, wherein the one or more reservable workspace stations are reservable to employees of the building.

12. One or more computer-readable storage media having computer-executable instructions stored thereon that, when executed by one or more processors, cause the one or more processors to perform operations comprising:
determining, by a processing circuit comprising one or more processors, a safety rule to be applied to a workspace comprising a plurality of workspace stations, the safety rule relating to limiting the transmission of the contagious disease, wherein the safety rule comprises a requirement that adjacent workstations or workstations within a threshold distance of one another must be unoccupied for the threshold amount of time for the workstations to be reservable;
receiving, at the processing circuit, a request for one or more reservable workspace stations, the request comprising one or more request parameters;
identifying the one or more reservable workspace stations from among the plurality of workspace stations by determining, by the processing circuit, whether to permit the one or more reservable workspace stations to be reserved based on the safety rule; and
generating, by the processing circuit, data identifying the one or more reservable workspace stations.

13. The media of claim 12, wherein receiving the request for one or more reservable workspace stations comprises receiving the request for one or more reservable workplace stations located in a location separate from the building, wherein the one or more reservable workspace stations are reservable to employees of the building.

14. The media of claim 12, wherein determining the safety rule to be applied to the workspace comprises determining a safety threshold based on at least one of:
a period of time since a hazardous incident has occurred at the workplace station,
a risk level associated with the contagious disease, and
an amount of sanitization that was performed at the one of the plurality of workplace station.

15. The media of claim 12, wherein:
the one or more request parameters comprises a timing parameter,
the safety rule comprises a threshold amount of time the workspace stations must be unoccupied after a last occupant; and
identifying the reservable workspace stations comprises determining that the workspace station has been unoccupied for at least the threshold amount of time.

16. The media of claim 12, wherein the one or more processors are further configured to:
generate the price for reserving the one or more reservable workspace stations;
provide the price and the one or more reservable workspace stations to a user interface;
receive, via the user interface, an input indicating a payment satisfying the price; and
in response to receiving the payment, satisfy the request to reserve the one or more reservable workplace stations.

17. The media of claim 16, wherein generating the price for reserving the one or more reservable workspace stations comprises:
receiving a plurality of bids for the one or more reservable workspace stations, wherein each of the plurality of bids is provided using a corresponding user interface; and
updating the price based on the number of received bids of the plurality of bids.

18. A system for mitigating risk of transmission of a contagious disease in a building, the system comprising a processing circuit comprising one or more processors and memory that, when executed by the one or more processors, causes the one or more processors to perform operations comprising:
determining a safety rule to be applied to a workspace comprising a plurality of workspace stations, the safety rule relating to limiting the transmission of the contagious disease;
receiving a request for one or more reservable workspace stations, the request comprising one or more request parameters;
identifying the one or more reservable workspace stations from among the plurality of workspace stations by determining, by the processing circuit, whether to permit the one or more reservable workspace stations to be reserved based on the safety rule, wherein determining whether to permit the workspace stations to be reserved based on the safety rule comprises:
determining that the one or more workspace stations are not reservable based on the safety rule; and
implementing an automated sanitizing feature or a notification to a building occupant to sanitize the one or more workspace stations such that the one or more workspace stations are reservable, wherein the automated sanitizing feature comprises at least one of sanitizing light or ultraviolet A (UVA) light, UVB light, or UVC light; and
generating data identifying the one or more reservable workspace stations.

19. The system of claim 18, wherein the processing circuit is further configured to:
generate, by the processing circuit, a price for reserving the one or more reservable workspace stations;
provide the price and the one or more reservable workspace stations to a user interface;
receive, via the user interface, an input indicating a payment satisfying the price; and
in response to receiving the payment, satisfy the request to reserve the one or more reservable workplace stations.

* * * * *